United States Patent [19]

Goodman et al.

[11] Patent Number: 4,994,368
[45] Date of Patent: Feb. 19, 1991

[54] AMPLIFICATION METHOD FOR POLYNUCLEOTIDE ASSAYS

[75] Inventors: Thomas C. Goodman, Mountain View; Martin Becker, Palo Alto; Edwin F. Ullman, Atherton; Samuel Rose, Mountain View, all of Calif.

[73] Assignee: Syntex (U.S.A.) Inc., Palo Alto, Calif.

[21] Appl. No.: 76,807

[22] Filed: Jul. 23, 1987

[51] Int. Cl.$^5$ .............. C12Q 1/68; C12P 19/34; G01N 33/566; G01N 33/48
[52] U.S. Cl. .............................. 435/6; 435/91; 436/501; 436/94
[58] Field of Search ............ 435/6, 91; 436/501, 436/94; 935/77, 78

[56] References Cited

U.S. PATENT DOCUMENTS

| | | | |
|---|---|---|---|
| 4,358,535 | 11/1982 | Falkow et al. | 435/5 |
| 4,423,153 | 12/1983 | Ranney et al. | 436/63 |
| 4,480,040 | 10/1984 | Owens et al. | 436/504 |
| 4,486,539 | 12/1984 | Ranki et al. | 436/504 |
| 4,490,472 | 12/1984 | Gottlieb | 436/504 |
| 4,656,134 | 4/1987 | Ringold | 435/91 |
| 4,663,283 | 5/1987 | Kleid et al. | 435/91 |
| 4,683,194 | 7/1987 | Saiki et al. | 935/78 |
| 4,800,159 | 1/1989 | Mullis et al. | 435/6 |
| 4,808,525 | 2/1989 | McClelland et al. | 435/91 |

FOREIGN PATENT DOCUMENTS

| | | |
|---|---|---|
| 904402 | of 0000 | Belgium . |
| 142299-A2 | 5/1985 | European Pat. Off. . |
| 0164054-A1 | 6/1985 | European Pat. Off. . |
| 0201184-A2 | 3/1986 | European Pat. Off. . |
| 0200362-A2 | 3/1986 | European Pat. Off. . |
| 0194545-A2 | 3/1986 | European Pat. Off. . |
| 184056-A2 | 6/1986 | European Pat. Off. . |
| 202688-A2 | 11/1986 | European Pat. Off. . |
| 229701-A2 | 7/1987 | European Pat. Off. . |
| 227976-A2 | 7/1987 | European Pat. Off. . |

OTHER PUBLICATIONS

Maniatis et al., Molecular Cloning-A Lab. Manual, Cold Spring Harbor Lab., 1982.
Chemical Abstract: vol. 106, No. 2, Jan. 12, 1987, Abstract No. 15257v, Chu et al.
Saiki et al., (1986) Science, 230: 1350-1354.
Langer, et al., (Proc. Natl. Acad. Science (U.S.A.), (1981) 78:6633-6637.
Brigati et al., Virology, (1983), vol. 126: pp. 32-50.

*Primary Examiner*—Robert A. Wax
*Assistant Examiner*—Stephanie W. Zitomer
*Attorney, Agent, or Firm*—Theodore J. Leitereg

[57] ABSTRACT

A method is disclosed for producing multiple copies of a primary polynucleotide sequence located at the 3' terminus of a polynucleotide. The method comprises (a) forming in the presence of nucleoside triphosphates and template-dependent polynucleotide polymerase an extension of a primary polynucleotide sequence hybridized with a template sequence of a single stranded pattern polynucleotide comprising two or more template sequences each containing one or more site specific cleavage sequences, (b) cleaving into fragments said extension at cleavable polynucleotide sequences in the presence of means for specifically cleaving said cleavable polynucleotide sequences when said extension is hybridized with said site specific cleavage sequences, (c) dissociating said fragments, (d) hybridizing said fragments with single stranded pattern polynucleotide, and repeating steps (a)-(d). Steps (a)-(d) may be conducted simultaneously or wholly or partially sequentially. The method may be applied in the detection of a polynucleotide analyte in a sample suspected of containing such analyte to facilitate such detection. Also disclosed are compositions for conducting the method of the invention.

68 Claims, 3 Drawing Sheets

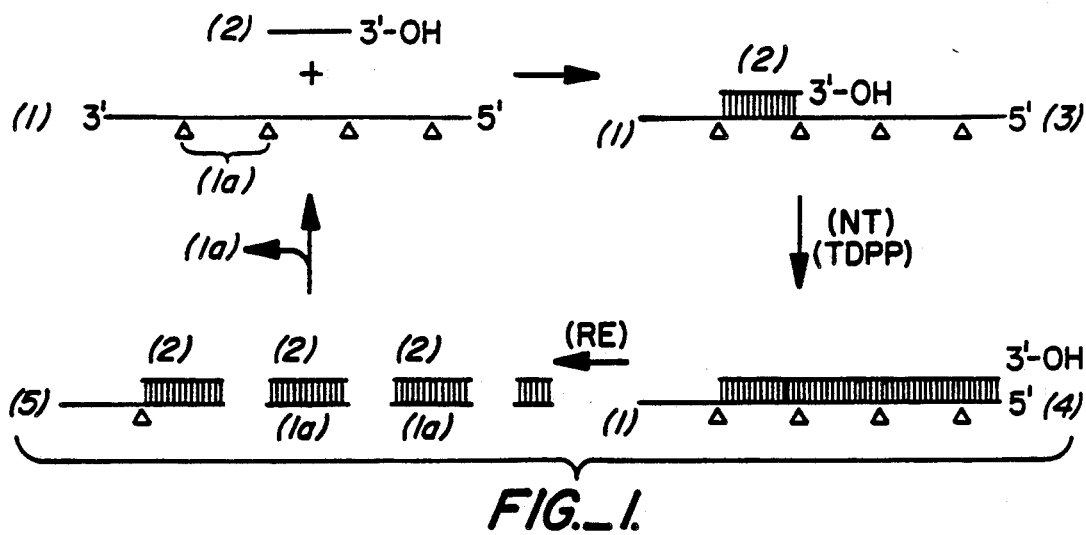
FIG._1.
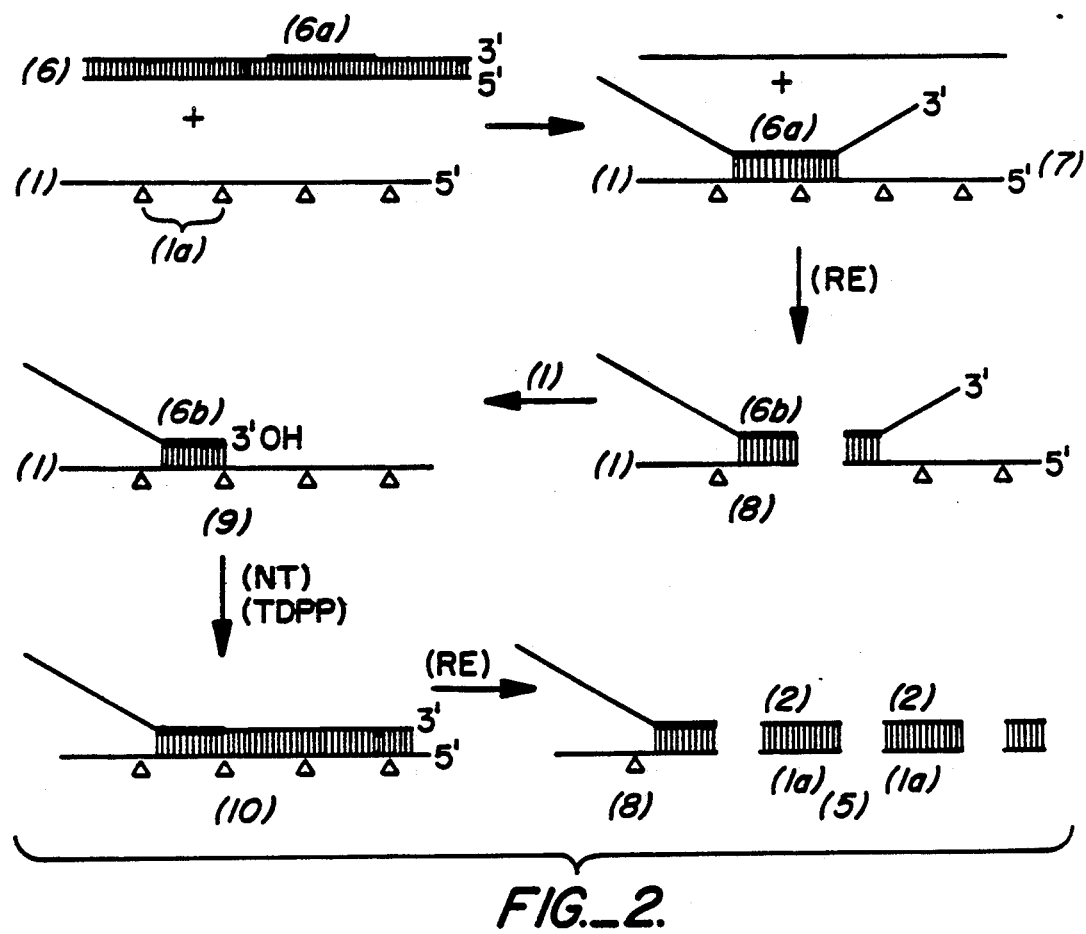
FIG._2.

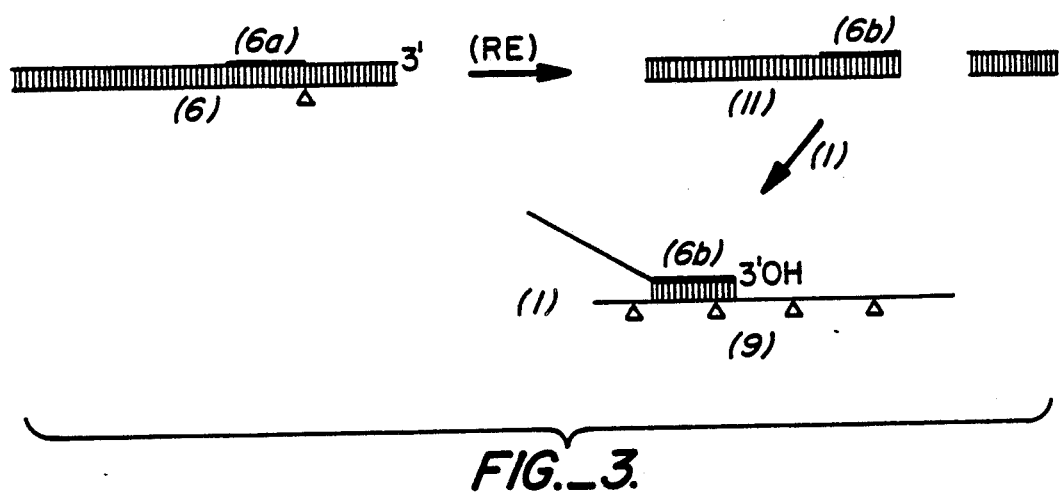
FIG._3.
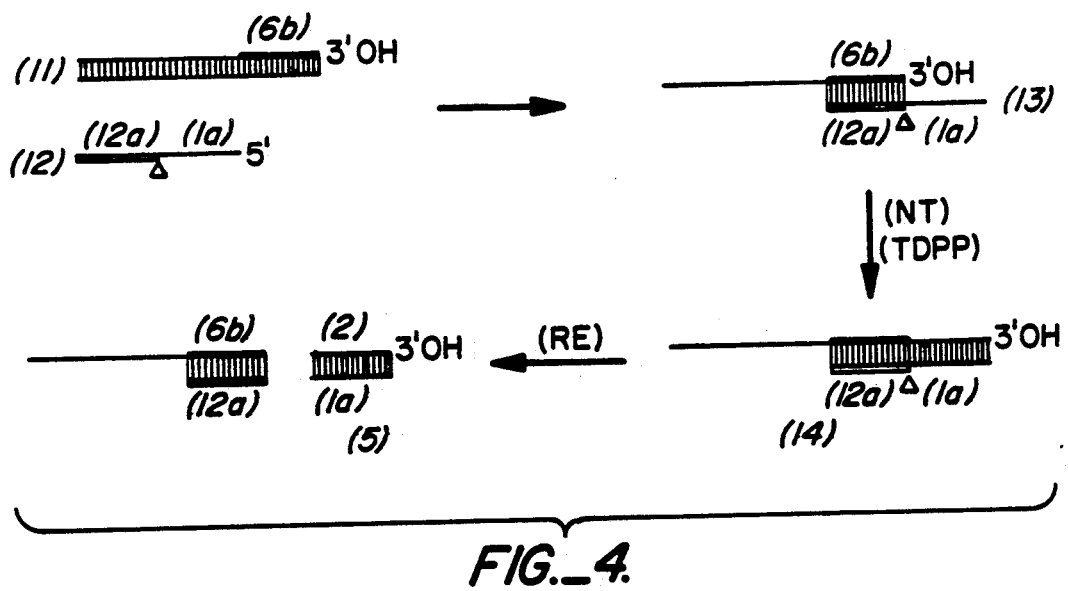
FIG._4.

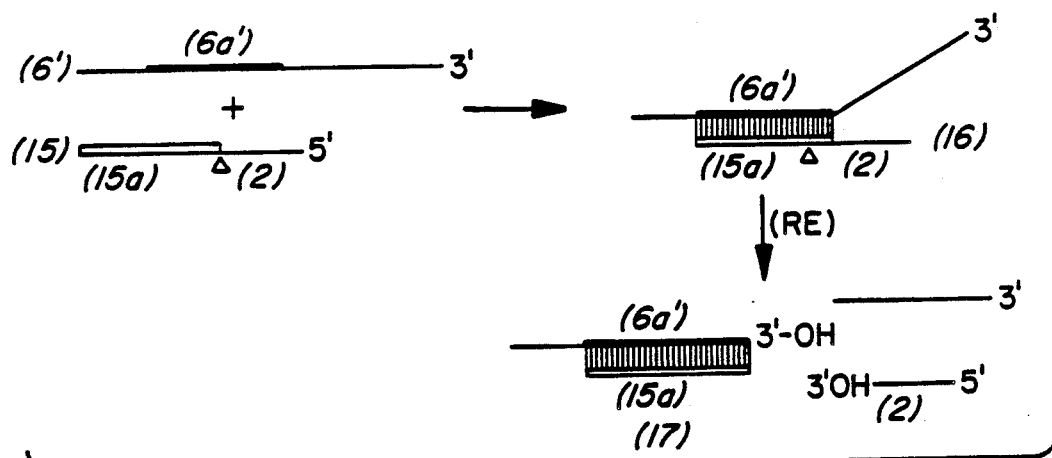
FIG._5.
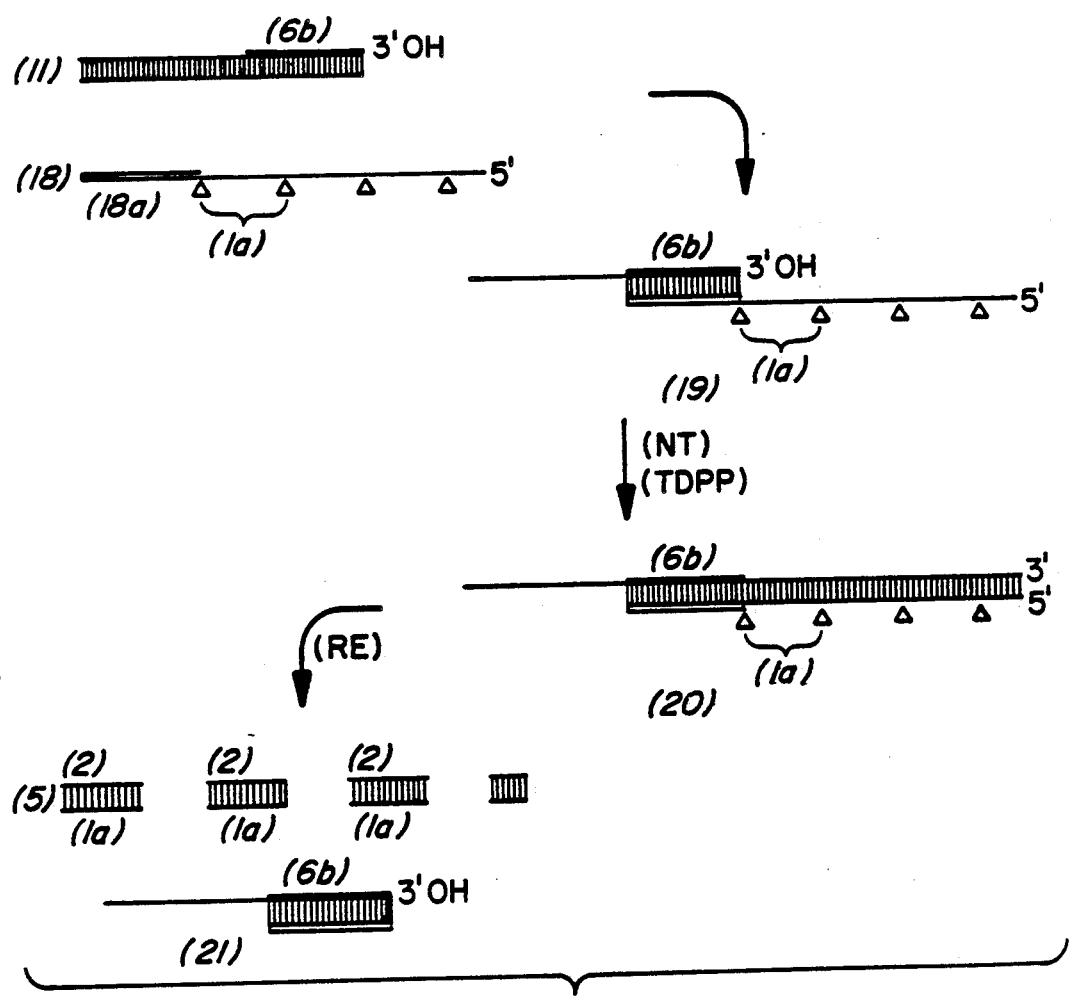
FIG._6.

AMPLIFICATION METHOD FOR POLYNUCLEOTIDE ASSAYS

BACKGROUND OF THE INVENTION

1. Field of the Invention.

Nucleic acid hybridization has been employed for investigating the identity and establishing the presence of nucleic acids. Hybridization is based on complementary base pairing. When complementary single stranded nucleic acids are incubated together, the complementary base sequences pair to form double stranded hybrid molecules. The ability of single stranded deoxyribonucleic acid (ssDNA) or ribonucleic acid (RNA) to form a hydrogen bonded structure with a complementary nucleic acid sequence has been employed as an analytical tool in molecular biology research. The availability of radioactive nucleoside triphosphates of high specific activity and the $^{32}P$ labelling of DNA with T4 kinase has made it possible to identify, isolate, and characterize various nucleic acid sequences of biological interest. Nucleic acid hybridization has great potential in diagnosing disease states associated with unique nucleic acid sequences. These unique nucleic acid sequences may result from genetic or environmental change in DNA by insertions, deletions, point mutations, or by acquiring foreign DNA or RNA by means of infection by bacteria, molds, fungi, and viruses. Nucleic acid hybridization has, until now, been employed primarily in academic and industrial molecular biology laboratories. The application of nucleic acid hybridization as a diagnostic tool in clinical medicine is limited because of the frequently very low concentrations of disease related DNA or RNA present in a patient's body fluid and the unavailability of a sufficiently sensitive method of nucleic acid hybridization analysis.

Current methods for detecting specific nucleic acid sequences generally involve immobilization of the target nucleic acid on a solid support such as nitrocellulose paper, cellulose paper, diazotized paper, or a nylon membrane. After the target nucleic acid is fixed on the support, the support is contacted with a suitably labelled probe nucleic acid for about two to forty-eight hours. After the above time period, the solid support is washed several times at a controlled temperature to remove unhybridized probe. The support is then dried and the hybridized material is detected by autoradiography or by spectrometric methods.

When very low concentrations must be detected, the current methods are slow and labor intensive, and nonisotopic labels that are less readily detected than radiolabels are frequently not suitable. A method for increasing the sensitivity to permit the use of simple, rapid, nonisotopic, homogeneous or heterogeneous methods for detecting nucleic acid sequences is therefore desirable.

Recently, a method for the enzymatic amplification of specific segments of DNA known as the polymerase chain reaction (PCR) method has been described. This in vitro amplification procedure is based on repeated cycles of denaturation, oligonucleotide primer annealing, and primer extension by thermophilic polymerase, resulting in the exponential increase in copies of the region flanked by the primers. The PCR primers, which anneal to opposite strands of the DNA, are positioned so that the polymerase catalyzed extension product of one primer can serve as a template strand for the other, leading to the accumulation of a discrete fragment whose length is defined by the distance between the 5' ends of the oligonucleotide primers.

2. Description of the Prior Art.

A process for amplifying, detecting and/or cloning nucleic acid sequences is disclosed in European patent applications 0 200 362 and 0 201 184. Sequence polymerization by polymerase chain reaction is described by Saiki, et al., (1986) *Science*, 230: 1350–1354. A method of making an oligonucleotide is described in European patent application no. 0194545 A2. Belgian patent application no. BE 904402 discloses a mold for making DNA detection probes. Gene amplification in eukaryotic cells is disclosed in U.S. Pat. No. 4,656,134.

Langer, et al., *Proc. Natl. Acad. Sci. USA*, (1981) 78: 6633–6637 discloses the enzymatic synthesis of biotin labelled polynucleotides and the use of these materials as novel nucleic acid affinity probes. The detection of viral genomes in cultured cells and paraffin embedded tissue sections using biotin labelled hybridization probes is discussed by Brigati, et al., *Virology*, (1983) 126: 32–50. U.S. Pat. No. 4,486,539 discloses the detection of microbial nucleic acids by a one step sandwich hybridization test. Sensitive tests for malignancies based on DNA detection is described in U.S. Pat. No. 4,490,472. U.S. Pat. No. 4,480,040 discloses the sensitive and rapid diagnosis of plant viroid diseases and viruses employing radioactively labelled DNA that is complementary to the viroid or to the nucleic acid of the virus being diagnosed. European patent application No. 83106112.2 (Priority U.S. patent application No. 391,440 filed June 23, 1982) teaches modified labelled nucleotides and polynucleotides and methods of preparing, utilizing, and detecting the same. Methods and compositions for the detection and determination of cellular DNA are disclosed in U.S. Pat. No. 4,423,153. Specific DNA probes in diagnostic microbiology are discussed in U.S. Pat. No. 4,358,535. A method for detection of polymorphic restriction sites and nucleic acid sequences is discussed in European patent application No. 0164054 A1. U.S. Pat. No. 4,663,283 describes a method of altering double-stranded DNA.

SUMMARY OF THE INVENTION

The invention disclosed herein includes methods and reagents for producing multiple copies of a primary polynucleotide sequence. This process can be initiated by the presence of a target polynucleotide sequence located at the 3' terminus of a polynucleotide. The method comprises: (a) forming in the presence of nucleoside triphosphates and template-dependent polynucleotide polymerase an extension of a primary polynucleotide sequence hybridized with a template sequence of a single stranded pattern polynucleotide comprising two or more template sequences each containing one or more site specific cleavage sequences, (b) cleaving into fragments the extension at cleavable polynucleotide sequences in the presence of means for specifically cleaving the polynucleotide sequences when the extension is hybridized with the site specific cleavage sequences, (c) dissociating the fragments, (d) hybridizing the fragments with single stranded pattern polynucleotide, and repeating steps (a)–(d) above. Steps (a)–(d) can be conducted simultaneously or wholly or partially sequentially.

The method and reagents have application in facilitating the determination of the presence of a polynucleotide analyte containing a target polynucleotide sequence in a sample suspected of containing such polynucleotide analyte. The target polynucleotide sequence can be DNA or RNA. In the analytical method, the target sequence is cut, e.g., by enzymes to provide a free 3'—OH when it does not already terminate in a 3'—OH. The target sequence is dissociated from any complementary nucleic acid and hybridized to a complementary binding sequence located at the 3' end of two or more template sequences in the single stranded pattern polynucleotide. Chain extension of the target sequence with nucleoside triphosphates and template dependent polynucleotide polymerase and cleavage of the cleavable polynucleotide sequence in the extension provides the primary polynucleotide sequences in this invention.

The invention further includes compositions for carrying out the above methods. One composition is a single stranded pattern polynucleotide that comprises an oligomer consisting of three to one-thousand monomeric units each consisting of an oligonucleotide template having from about eight to one-hundred bases and at least one restriction site. The monomeric units are preferably but need not be identical. The oligomer may be substituted at the 3'-end with a binding sequence complementary to a target sequence, and the 3'-terminal nucleotide will preferably be substituted by a chemical functionality that prevents a chain extension reaction with a template dependent polynucleotide polymerase. Alternatively, the single stranded pattern polynucleotide may be a ring. When the present method and compositions are untilized to determine the presence of a polynucleotide analyte in a sample, the cleaved fragments are detected by any means for detecting DNA fragments. The presence of the fragment or a complementary fragment indicates the presence of the polynucleotide analyte in the sample.

BRIEF DESCRIPTION OF THE DRAWINGS

FIG. 1 depicts a method for obtaining multiple copies of a primary polynucleotide sequence in accordance with the present invention.

FIG. 2 depicts a method for effecting formation of a primary polynucleotide sequence in response to the presence of a polynucleotide analyte in accordance with the present invention.

FIGS. 3-6 depict alternative methods for effecting formation of a primary polynucleotide sequence by the presence of a polynucleotide analyte.

DESCRIPTION OF THE SPECIFIC EMBODIMENTS

The present method allows the production of multiple copies of a primary polynucleotide sequence. The formation of the primary polynucleotide sequence can be initiated by the presence of a target polynucleotide sequence located at the 3'-terminus of a polynucleotide and is useful in detection of such a target sequence. The target polynucleotide sequence may be present in a polynucleotide analyte in a sample suspected of containing the analyte. The primary polynucleotide sequence may be the same as, but is preferably different from, the target polynucleotide sequence. In the production of multiple copies of a primary polynucleotide sequence the following components are provided: (i) the primary polynucleotide sequence, (ii) a single stranded pattern polynucleotide comprising two or more template sequences each containing one or more site specific cleavage sequences, (iii) nucleoside triphosphates, (iv) template-dependent polynucleotide polymerase, and (v) means for specifically cleaving cleavable polynucleotide sequences when an extension of the primary polynucleotide sequence is hybridized with the site specific cleavage sequences. The template sequence is complementary to and can hybridize with the primary polynucleotide sequence. The complex of the primary polynucleotide sequence with the single stranded pattern polynucleotide is incubated either simultaneously or wholly or partially sequentially with remaining components under conditions for either simultaneously or wholly or partially sequentially forming the extension of the primary polynucleotide sequence comprising one or more copies of the primary polynucleotide sequence connected through the cleavable polynucleotide sequences, cleaving the extension into fragments at the cleavable polynucleotide sequences, dissociating the complex of the template sequence and the cleaved primary polynucleotide sequence which is identical with the primary polynucleotide sequence, and reforming the complex of the primary polynucleotide sequence with the single stranded pattern polynucleotide which is usually in excess. The above steps are repeated until the desired number of copies are obtained.

The target polynucleotide sequence can be part of a polynucleotide analyte that is to be detected. One aspect of the invention comprises a determination of such a polynucleotide analyte by causing the target polynucleotide sequence to initiate the above described method for producing multiple copies. In this method the target polynucleotide sequence in the polynucleotide analyte is caused to terminate in a 3' hydroxyl group when it is not already so terminated. This is usually effected by incubation with a restriction endonuclease. The target sequence is dissociated from complementary polynucleotides and caused to hybridize with the single stranded pattern polynucleotide which has a complementary binding polynucleotide sequence bound at the 3' end of the template sequence. The formation of multiple copies of the primary polynucleotide sequence is then carried out by an extension of the target sequence along the single stranded pattern polynucleotide and cleavage of the extension into fragments as described above for the hybrid of the primary polynucleotide sequence with the single stranded pattern polynucleotide. The cleaved fragments are detected, and their presence indicates the presence of the polynucleotide analyte in the sample. The hybridization, chain extension, and cleaving can be repeated until the single stranded polynucleotide or nucleoside triphosphates are exhausted or the template-dependent polynucleotide polymerase becomes inactive, but will preferably not be repeated after the ratio of the cleaved fragments induced by the target polynucleotide sequence to those non-specifically induced ceases to increase. The present method has application to the detection of both DNA and RNA sequences.

One composition of the present invention is a single stranded pattern polynucleotide that comprises an oligomer consisting of three to one-hundred monomeric units. Each monomeric unit consists of an identical oligodeoxynucleotide template having from about eight to one hundred, preferably 10 to 100, bases and at least one restriction site. Preferably, the oligomer is substituted at the 3' end by a binding polynucleotide sequence of 15 or more bases that is complementary to a target polynucleotide sequence. The single stranded pattern polynucleotide is substituted at the 3' end with a chemical functionality that prevents chain extension with a template dependent polynucleotide polymerase, or is cyclic.

Before proceeding further with a description of the specific embodiments of the present invention, a number of terms will be defined.

Polynucleotide analyte—a compound or composition to be measured which is a polymeric nucleotide having about 20 to 500,000 or more nucleotides, usually about 100 to 200,000 nucleotides, more frequently 500 to 15,000 nucleotides. The polynucleotide analytes include nucleic acids from any source in purified or unpurified form including DNA (dsDNA and ssDNA) and RNA, including t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like. The polynucleotide analyte can be only a minor fraction of a complex mixture such as a biological sample. The analyte can be obtained from various biological material by procedures well known in the art. Some examples of such biological material by way of illustration and not limitation are disclosed in Table I below.

TABLE I

| Microorganisms of interest include | |
|---|---|
| Corynebacteria | |
| *Corynebacterium diptheria* | |
| Pneumococci | |
| *Diplococcus pneumoniae* | |
| Streptococci | |
| *Streptococcus pyrogenes* | |
| *Streptococcus salivarus* | |
| Staphylococci | |
| *Staphylococcus aureus* | |
| *Staphylococcus albus* | |
| Neisseriae | |
| *Neisseria meningitidis* | |
| *Neisseria gonorrhea* | |
| Enterobacteriaciae | |
| *Escherichia coli* | The colliform bacteria |
| *Aerobacter aerogenes* | |
| *Klebsiella pneumoniae* | |
| *Salmonella typhosa* | The Salmonellae |
| *Salmonella choleraesuis* | |
| *Salmonella typhimurium* | |
| *Shigella dysenteria* | The Shigellae |
| *Shigella schmitzii* | |
| *Shigella arabinotarda* | |
| *Shigella flexneri* | |
| *Shigella boydii* | |
| *Shigella sonnei* | |
| Other enteric bacilli | |
| *Proteus vulgaris* | Proteus species |
| *Proteus mirabilis* | |
| *Proteus morgani* | |
| *Pseudomonas aeruginosa* | |
| *Alcaligenes faecalis* | |
| *Vibrio cholerae* | |
| Memophilus-Bordetella group | *Rhizopus oryzae* |
| *Hemophilus influenza. H. ducryi* | *Rhizopus arrhizua* Phycomycetes |
| *Hemophilus hemophilus* | *Rhizopus nigricans* |
| *Hemophilus aegypticus* | *Sporotrichum schenkii* |
| *Hemophilus parainfluenzae* | *Flonsecaea pedrosoi* |
| *Bordetella pertussis* | *Flonsecaea compact* |
| Pasteurellae | *Fonsecacea dermatidis* |
| *Pasteurella pestis* | *Cladosporium carrionii* |
| *Pasteurella tulareusis* | *Phialophora verrucosa* |

TABLE I-continued

| Microorganisms of interest include | |
|---|---|
| Brucellae | *Aspergillus nidulans* |
| *Brucella melitensis* | *Madurella mycetomi* |
| *Brucella abortus* | *Madurella grisea* |
| *Brucella suis* | *Allescheria boydii* |
| Aerobic Spore-forming Bacilli | *Phialophora jeanselmei* |
| *Bacillus anthracis* | *Microsporum gypseum* |
| *Bacillus subtilis* | *Trichophyton mentagrophytes* |
| *Bacillus megaterium* | *Keratinomyces ajelloi* |
| *Bacillus cereus* | *Microsporum canis* |
| Anaerobic Spore-forming Bacilli | *Trichophyton rubrum* |
| *Clostridium botulinum* | *Microsporum adouini* |
| *Clostridium tetani* | Viruses |
| *Clostridium perfringens* | Adenoviruses |
| *Clostridium novyi* | Herpes Viruses |
| *Clostridium septicum* | *Herpes simplex* |
| *Clostridium nistolyticum* | Varicella (Chicken pox) |
| *Clostridium tertium* | *Herpes Zoster* (Shingles) |
| *Clostridium bifermentans* | Virus B |
| *Clostridium sporogenes* | Cytomegalovirus |
| Mycobacteria | Pox Viruses |
| *Mycobacterium tuberculosis hominis* | Variola (smallpox) |
| *Mycobacterium bovis* | Vaccinia |
| *Mycobacterium avium* | *Poxvirus bovis* |
| *Mycobacterium leprae* | Paravaccinia |
| *Mycobacterium paratuberculosis* | *Molluscum contagiosum* |
| Actinomycetes | Picornaviruses |
| (fungus-like bacteria) | |
| *Actinomyces Isaeli* | Poliovirus |
| *Actinomyces bovis* | Coxsackievirus |
| *Actinomyces naeslundii* | Echoviruses |
| *Nocardia asteroides* | Rhinoviruses |
| *Nocardia brasiliensis* | Myxoviruses |
| The Spirochetes | Influenza (A, B, and C) |
| *Treponema pallidum* | Parainfluenza (1–4) |
| *Spirillum minus* | |
| *Treponema pertenue* | Mumps Virus |
| *Strepto-bacillus monoiliformis* | Newcastle Disease Virus |
| *Treponema carateum* | Measles Virus |
| *Borrelia recurrentis* | Rinderpest Virus |
| *Leptospira icterohemorrhagiae* | Canine Distemper Virus |
| *Leptospira canicola* | Respiratory Syncytial Virus |
| Trypanasomes | Rubella Virus |
| Mycoplasmas | Arboviruses |
| *Mycoplasma pneumoniae* | |
| Other pathogens | Eastern Equine Eucephalitis Virus |
| *Listeria monocytogenes* | Western Equine Eucephalitis Virus |
| *Erysipelothrix rhusiopathiae* | Sindbis Virus |
| *Streptobacillus moniliformis* | Chikugunya Virus |
| *Donvania granulomatis* | Semliki Forest Virus |
| *Bartonella bacilliformis* | Mayora Virus |
| Rickettsiae (bacteria-like parasites) | St. Louis Encephalitis Virus |
| *Rickettsia prowazekii* | California Encephalitis Virus |
| *Rickettsia mooseri* | Colorado Tick Fever Virus |
| *Rickettsia rickettsii* | Yellow Fever Virus |
| *Rickettsia conori* | Dengue Virus |
| *Rickettsia australis* | Reoviruses |
| *Rickettsia sibiricus* | Reovirus Types 1–3 |
| | Retroviruses |
| *Rickettsia akari* | Human Immunodeficiency Viruses (HIV) |
| *Rickettsia tsutsugamushi* | Human T-cell Lymphotrophic Virus I & II (HTLV) |
| *Rickettsia burnetti* | Hepatitis |
| *Rickettsia quintana* | Hepatitis A Virus |
| Chlamydia (unclassifiable parasites bacterial/viral) | Hepatitis B Virus |
| Chlamydia agents (naming uncertain) | Hepatitis nonA-nonB Virus Tumor Viruses |
| Fungi | |
| *Cryptococcus neoformans* | Rauscher Leukemia Virus |
| *Blastomyces dermatidis* | Gross Virus |
| *Hisoplasma capsulation* | Maloney Leukemia Virus |

TABLE I-continued

Microorganisms of interest include

Coccidioides immitis
Paracoccidioides brasiliensis
Candida albicans
Aspergillus fumigatus
Mucor corymbifer (Absidia corymbifera)

Human Papilloma Virus

The polynucleotide analyte, where appropriate, will be treated to cleave the analyte to obtain a fragment that contains a target polynucleotide sequence located at the 3' end of a polynucleotide. Accordingly, the analyte can be cleaved by known techniques such as treatment with a restriction endonuclease or other site specific chemical cleavage methods. Such treatment must produce a terminal 3'-hydroxy group or a group convertible to a 3'-hydroxyl group.

For purposes of this invention, the cleaved fragment obtained from the polynucleotide analyte will usually be at least partially denatured or single stranded or treated to render it denatured or single stranded. Such treatments are well known in the art and include, for instance, heat or alkali treatment. For example, double stranded DNA can be heated at 90°-100° C. for a period of about 1 to 10 minutes to produce denatured material.

Target polynucleotide sequence—at least a portion of a sequence of nucleotides to be identified, the identity of which is known to an extent sufficient to allow preparation of a binding polynucleotide sequence that is complementary to and will hybridize with such target sequence. The target polynucleotide sequence usually will contain from about 12 to 1000 or more nucleotides, preferably 15 to 50 nucleotides. The target polynucleotide sequence terminates or can be caused to terminate in a 3'-hydroxyl group and is frequently a part of the polynucleotide analte. The target polynucleotide sequence will generally be a fraction of a larger molecule or it may be substantially the entire molecule. The minimum number of nucleotides in the target polynucleotide sequence will be selected to assure that the presence of polynucleotide analyte in a sample will provide at least double the number of copies of target polynucleotide sequence that would be expected to occur by chance in a sample that does not contain the polynucleotide analyte. In general, the number of copies expected to occur by chance will be $LG/4^n$ although the frequency of occurrence of a specific sequence in a sample may be greater or less than expected by chance. In this expression n is the number of nucleotides in the target polynucleotide sequence, L is the number of base pairs in the genome of the biologic source of the sample, and G is the number of genomic copies present in the sample. The maximum number of nucleotides in the target sequence will normally be governed by the length of the polynucleotide analyte and its tendency to be broken by shearing, by endogenous nucleases or by reagents used to cleave the target sequence.

The target polynucleotide sequence will normally be part of the polynucleotide analyte. When not part of the analyte, the target polynucleotide sequence will be provided as part of a polynucleotide at a location other than at the 3' end of the polynucleotide. The presence of the polynucleotide analyte will then cause the target sequence to be cut causing it to terminate at the 3'end. For example, the polynucleotide analyte can be RNA that can be hybridized with a complementary single stranded primer polynucleotide containing the target polynucleotide sequence that includes a cleavage site. The hybridized RNA: primer molecule can be treated with a cleavage agent such as a restriction endonuclease capable of cutting heteroduplexes and then denatured to provide a single stranded target sequence terminating in a 3'—OH group.

Primary polynucleotide sequence—a polynucleotide sequence that can be the same as or different from the target polynucleotide sequence and will usually be different. The primary polynucleotide sequence is complementary to the template sequence. It will normally be a sequence of eight to 100 bases, usually DNA, preferably 10-75 bases, more preferably 12-50 bases. Frequently, the primary polynucleotide sequence will contain derivatized nucleotides, and it will preferably consist of only two or three of the four nucleotides A and dA or derivatives thereof, U and dT or derivatives thereof, C and dC and derivatives thereof, and G and dG or derivatives thereof. Multiple copies of the primary polynucleotide sequence will be produced in the present method as a result of the presence of the target polynucleotide sequence.

Single stranded pattern polynucleotide—a natural or synthetic sequence of nucleotides that is capable of hybridizing with the primary polynucleotide sequence. The single stranded pattern polynucleotide comprises an oligomer of two or more template sequences, preferably two or more copies, preferably at least three, of a template sequence, preferably identical, each containing one or more site specific cleavage sequences. The template sequence can contain two or three, preferably three, members selected from the group comprising nucleotides, deoxynucleotides, and derivatives thereof. For example, the template sequence can preferably consist of only three of the four nucleotides A and dA or derivatives thereof, U and dT or derivatives thereof, C and dC or derivatives thereof, and G and dG or derivatives thereof. The template sequence is complementary to the primary polynucleotide sequence. The oligomer can be attached at its 3' end directly or through intermediate nucleotides to the 5' end of a binding polynucleotide sequence complementary or substantially complementary to the target polynucleotide sequence. Usually, the attachment of the oligomer to the binding polynucleotide sequence will be through one or more site specific cleavage sequences. When the oligomer is bound to the binding polynucleotide sequence through intermediate nucleotides and consists of only two or three bases, the intermediate nucleotides will also be selected from those bases. The single stranded pattern polynucleotide can also contain nucleotides other than those in the binding polynucleotide sequence and the template sequences as long as such nucleotides do not interfere with the present method. Such other nucleotides would usually be outside the binding polynucleotide sequence and the oligomer.

The single stranded pattern polynucleotide will usually contain from 36 to 4,000 nucleotides, preferably 80 to 1,000 nucleotides and will preferably contain 3 to 100 template polynucleotide sequences. The single stranded pattern polynucleotide can be DNA or RNA, preferably DNA, and can be linear or circular, preferably circular. It can be a synthetic oligonucleotide or constructed from a virus, plasmid, or the like. When not cyclic it will usually be terminated at its 3' end by a group that will interfere with chain extension by nucleic acid polymerases.

A critical feature of the single stranded pattern polynucleotide sequence is that it be free from any polynucleotide sequence that is either complementary or can form an extension along the single stranded pattern polynucleotide sequence that is complementary to the template or binding polynucleotide sequences. Furthermore, where the single stranded pattern polynucleotide sequence is non-cyclic, it is preferably terminated at the 3' end with a group incapable of reacting in a chain extension reaction sequence by template-dependent polynucleotide polymerase. In this way random initiation of chain extension along the template is prevented. Exemplary of such a group, by way of illustration and not limitation, are dideoxynucleotides, such as dideoxythymidine, dideoxyadenosine, dideoxyguanosine, and dideoxycytidine, isopropylphosphoryl, phosphate, N-(trimethyl ammonium ethyl) carbamoyl, polysaccharides such as dextran, polystrene, hydrazones, proteins, and deoxyribose-3'-phosphoryl and the like.

Dideoxynucleotide capping can be carried out according to conventional techniques such as, described by Atkinson, et al. (1969) *Biochem.,* 8: 4897–4904. Hydrazone formation can be obtained by oxidation of a ribonucleotide at the 3' end with periodate to form a dialdehyde, which can then react with substituted hydrazines such as dinitrophenylhydrazine, positively charged hydrazines such as 2-trimethylammonium-1-ethylhydrazine, hydrazines bonded to dextran and proteins, particularly hydrazide derivatives of carboxyalkyldetrans and proteins, etc., and the like. Such 3' blocked material may then be separated from other reaction mixture components by affinity chomatography and other techniques well known in the art. Aldehyde formation followed by derivatization of the aldehyde is one general procedure for blocking the 3' end of the template. See, for example, Reines, et al. (1974) *Nucleic Acids Research,* 1:767–786. A 3'-terminal phosphate group can be achieved, for example, by treating the single stranded polynucleotide terminated with a ribonucleotide with periodate and β-elimination by cyclohexylamine or benzylamine (See Krynetskaya et al. (1986) *Nucleosides and Nucleotides,* 5(1): 33–43 or by T4 RNA ligase addition of pCp (3',5'-diphosphate cytidine) such as is typically carried out in the 3' end labelling of DNA.

Terminal 3' blocking may also be achieved by covalent attachment of the 3' end to a glass bead, resin, or any other suitably modified particle or bead. This means of blocking the 3' functionality is commonly practiced under a number of forms in the synthesis of oligonucleotides.

A specific embodiment of a single stranded pattern polynucleotide that can be utilized in the present invention is one in which the oligomer consists of only three nucleotide members selected from the group consisting of dA, dC, dG and dT or derivatives of these nucleotide members that have similar complementarity of binding to nucleotide bases as the parent member and do not interfere with template dependent polynucleotide polymerases, when incorporated in the template polynucleotide sequence.

The single stranded pattern polynucleotide can be obtained by cloning or synthesis. Synthetic procedures and isolation methods can be automated or not. Such methods include phosphotriester and phosphodiester methods (Narang, et al. (1979) *Meth. Enzymol* 68:90) and synthesis on a support (Beaucage, et al. (1981) *Tetrahedron Letters* 22:1859–1862) as well as the phosphoramidite technique and others described in "Synthesis and Applications of DNA and RNA," S. A. Narang, editor, Academic Press, New York, 1987, and the references contained therein.

Template sequence—a sequence of nucleotides, at least one of which is complementary to the primary polynucleotide sequence, located within the single stranded pattern polynucleotide and present usually as a tandem repeat including one or more site specific cleavage sequences. The number of nucleotides in the template sequence should be sufficiently high that stringency conditions used to hybridize with the primary polynucleotide sequence will prevent excessive random non-specific hybridization and not so high that the conditions needed to dissociate the template sequence from the primary polynucleotide sequence will inactivate the template dependent polynucleotide polymerase. Usually, the number of nucleotides in the template sequence is from 8 to 100, preferably, 10 to 75, more preferably, 12 to 30. Usually, from about three to 100 copies of the template sequence are present in the single stranded pattern polynucleotide.

Site specific cleavage sequence—a sequence of nucleotides in a polynucleotide that, when complexed with a complementary polynucleotide having a cleavable polynucleotide sequence, will promote cleavage of such complementary cleavable polynucleotide sequence at a specific site within the sequence. An additional reagent will usually be required for cleavage. The site specific cleavage sequence will usually consist of 4 to 30 nucleotides, more usually 4 to 15 nucleotides, preferably 4 to 8 nucleotides. Normally, the complex of the site specific cleavage sequence and the polynucleotide having the cleavable polynucleotide sequence will comprise a restriction endonuclease site and the additional reagent will be a restriction endonuclease.

Type I restriction endonucleases recognize a specific nucleotide sequence and make a cut nearby, without any specificity as to the nucleotide sequence that is cut. Consequently, utilization of a cleavage promoting sequence recognized by a Type I restriction endonuclease would require the use of a second reagent or the presence of a derivatized nucleotide in the site specific cleavage sequence that would provide for cleavage at a specific site. Type II restriction endonucleases recognize a specific sequence and make a double strand cut at a fixed point within that sequence. Such sequences usually have a central axis of symmetry and read identically in both directions from that axis. Type II restriction endonucleases are of most general utility in the method of the invention. Type III restriction enzymes recognize asymmetric restriction sites that are a specific sequence and make a double strand cut at a fixed point some number of nucleotides to the side of such sequence. Type III enzymes are therefore also of use in this method.

By way of illustration and not limitation some exemplary nucleotide sequences and the restriction endonucleases that recognize them are set out in Table II below and in Kassler and Höltke (1986) *Gene* 47:1–153 and Roberts (1987) *Nucleic Acids Res.* 15:r189–r217, and references contained therein.

TABLE II

| Restriction Site | Restriction Endonuclease |
| --- | --- |
| (5'...3') | |
| GACGT\|C | Aat II |
| GT\|AGAC | Acc I |

TABLE II-continued

| Restriction Site | Restriction Endonuclease |
|---|---|
| \|CT | |
| GPu\|CGPyC | Aha II |
| AG\|CT | Alu I |
| GGGCC\|C | Apa I |
| C\|PyCGPuG | Ava I |
| G\|GACC | Ava II |
| T | |
| TGG\|CCA | Bal I |
| G\|GATCC | BamH I |
| G\|GPyPuCC | Ban I |
| GPuGCPy\|C | Ban II |
| GCAGC(N)8\| | Bbv I |
| T\|GATCA | Bcl I |
| GCCNNNN\|NGGC | Bgl I |
| A\|GATCT | Bgl II |
| GAATGCN\| | Bsm I |
| G C | Bsp 1286 |
| GAGCA\|C | |
| T T | |
| G\|CGCGC | BssH II |
| G\|GTNACC | BstE II |
| CC\|AGG | BstN I |
| T | |
| CCANNNNN\|NTGG | BstX I |
| AT\|CGAT | Cla I |
| C\|TNAG | Dde I |
| CH3 | |
| GA \|TC | Dpn I |
| TTT\|AAA | Dra I |
| G\|AATTC | EcoR I |
| GAT\|ATC | EcoR V |
| CG\|CG | FnuD II |
| CG\|NGC | Fnu4HI |
| GGATG(N)9\| | Fok I |
| TGC\|GCA | Fsp I |
| PuGCGC\|Py | Hae II |
| GG\|CC | Hae III |
| GACGC(N)5\| | Hga I |
| T T | |
| GAGCA\|C | HgiAI |
| GCG\|C | Hha I |
| GTPy\|PuAC | Hinc II |
| A\|AGCTT | Hind III |
| G\|ANTC | Hinf I |
| G\|CGC | HinP I |
| GTT\|AAC | Hpa I |
| C\|CGG | Hpa II |
| GGTGA(N)8\| | Hph I |
| GGTAC\|C | Kpn I |
| \|GATC | Mbo I |
| GAAGA(N)8\| | Mbo II |
| A\|CGCGT | Mlu I |
| CCTC(N)7\| | Mnl I |
| C\|CGG | Msp I |
| CC\|TNAGG | Mst II |
| GCC\|GGC | NaeI |
| GG\|CGCC | Nar I |
| C | Nci I |
| CC\|GGG | |
| C\|CATGG | Nco I |
| CA\|TATG | Nde I |
| G\|CTAGC | Nhe I |
| CATG\| | Nla III |
| GGN\|NCC | Nla IV |
| GC\|GGCCGC | Not I |
| TCG\|CGA | Nru I |
| ATGCA\|T | Nsi I |
| C\|TCGAG | PaeR7 I |
| CTGCA\|G | Pst I |
| CGAT\|CG | Pvu I |
| CAG\|CTG | Pvu II |
| GT\|AC | Rsa I |
| GAGCT\|C | Sac I |
| CCGC\|GG | Sac II |
| G\|TCGAC | Sal I |
| \|GATC | Sau3A I |
| G\|GNCC | Sau96 I |
| AGT\|ACT | Sca I |
| CC NGG | ScrF I |
| GCATC(N)5 | Sfa N I |
| GGCCNNNN\|NGGCC | Sfi I |
| CCC\|GGG | Sma I |
| TAC\|GTA | SnaB I |
| A\|CTAGT | Spe I |
| GCATG\|C | Sph I |
| AAT\|ATT | Ssp I |
| AGG\|CCT | Stu I |
| AA | Sty I |
| C\|CTTGG | |
| T\|CGA | Taq I |
| GACN\|NNGTC | TthIII I |
| T\|CTAGA | Xba I |
| C\|TCGAG | Xho I |
| Pu\|GATCPy | Xho II |
| C\|CCGGG | Xma I |
| C\|GGCCG | Xma III |
| GAANN\|NNTTC | Xmn I |

The site specific cleavage sequence will frequently be cut but is not required to be cut during the method of the present invention as long as the reagent required for cleavage is capable of cleaving a cleavable polynucleotide sequence in a polynucleotide that is complementary and bound to the specific cleavage sequence. Exemplary of such a site specific cleavage sequence is a methylated sequence corresponding to one of those given above in Table II. Methylation of the site specific cleavage sequences of the single stranded pattern polynucleotide can be achieved by introducing a methylated nucleotide in the synthesis of the single stranded pattern polynucleotide or by using an enzyme such as methyl transferase, or the like. To achieve cleavage of the sequence complementary to the site specific cleavage sequence of the single stranded pattern polynucleotide after chain extension in accordance with the present method, a cleaving agent that recognizes and cleaves hemi-methylated sites is employed. For example, an enzyme such as Taq I which can cut the unmethylated strand of $$TCG^{6mA}|/TCGA$$

duplexes or Sau 3AI, MspI, AccI or Xho II or the like can be employed. Nelson and McClelland (1987) *Nucleic Acids Res.* 15, r219–r230 and the references contained therein. Another example of a cleavable sequence formed during the method of the invention is a DNA sequence produced utilizing an RNA template sequence or a RNA sequence produced utilizing a DNA template sequence wherein the cleaving agent cleaves only RNA or DNA, a DNA/RNA hybrid, as the case may be. Cleavage of DNA and possibly RNA also in a DNA:RNA hybrid has been described by Molloy and Symms (1980) *Nucleic Acids Res.* 8, 2939–2946.

Nucleoside triphosphates—a nucleoside having a 5' triphosphate substituent, usually a deoxynucleoside triphosphate. The nucleosides are pentose sugar derivatives of nitrogenous bases of either purine or pyrimidine derivation, covalently bonded to the 1'-carbon of the pentose sugar. The purine bases include adenine (A), guanine (G), and derivatives and analogs thereof. The pyrimidine bases include cytosine (C), thymine (T), uracil (U), and derivatives and analogs thereof.

The derivatives and analogs are exemplified by those that are recognized and polymerized in a similar manner to the underivatized nucleotide triphosphates. Examples of such derivatives or analogs by way of illustration and not limitation are those which are modified with a reporter group, biotinylated, amine modified, radiolabeled, alkylated, and the like and also include thiophosphate, phosphite, ring atom modified derivatives, and the like. The reporter group can be a fluorescent group such as fluoroscein, a chemiluminescent group such as luminol, a terbium chelator such as N-(hydroxyethyl) ethylenediaminetriacetic acid that is capable of detection by delayed fluorescence, and the like.

Template-dependent polynucleotide polymerase (TDPP)—a catalyst, usually an enzyme, for forming an extension of the primary polynucleotide sequence or the target polynucleotide sequence, as the case may be, along the single stranded pattern polynucleotides where the extension is complementary to the template sequence. The template-dependent polynucleotide polymerase utilizes the nucleoside triphosphates as the building blocks for the extension which proceeds in a 5' to 3' (3' to 5' with respect to the template) direction until extension terminates. Usually, the catalysts are enzymes, such as RNA polymerases, preferably DNA polymerases such as, for example, prokaryotic DNA polymerase (I, II, or III), T4 DNA polymerase, T7 DNA polymerase, Klenow fragment, reverse transcriptase, RNA replicases, and the like derived from any source such as cells, bacteria, such as *E. coli*, plants, animals, virus, thermophilic bacteria, and so forth.

Means for specifically cleaving a cleavable polynucleotide sequence when the cleavable polynucleotide sequence is hybridized with a complementary polynucleotide having a site specific cleavage sequence—usually a catalyst. When the cleavable polynucleotide sequence is a restriction endonuclease recognition site, such means is usually a restriction endonuclease, which is an enzyme capable of cutting double strand DNA at or near a particular nucleotide sequence. Such means can also be a chemical compound that specifically reacts with a base resulting in cleavage. See, for example, Peter Dervan (1986) *Science* 232:464–471. Cleavage of a specific sequence may also be achieved by incorporating in the site specific cleavage sequences a cleavage promoting group such as a chelate iron atom or a photoactivator.

Wholly or partially sequentially—when the sample and various agents utilized in the present invention are combined other than simultaneously, one or more may be combined with one or more of the remaining agents to form a subcombination. Each subcombination can then be subjected to one or more steps of the present method. Thus, each of the subcombinations can be incubated under conditions to achieve one or more of the desired results.

One embodiment of the method of the present invention is directed to the production of multiple copies of a primary polynucleotide sequence as the result of the presence of a target polynucleotide sequence substantially identical to the primary polynucleotide sequence located at the 3' terminus of a polynucleotide. A combination is prepared either wholly or partially sequentially or simultaneously comprising the target polynucleotide sequence, single stranded pattern polynucleotide, nucleotide triphosphates, template-dependent polynucleotide polymerase, and means for specifically cleaving cleavable polynucleotide sequences. The combination is incubated under conditions for either wholly or partially sequentially or simultaneously hybridizing the target sequence with single stranded pattern polynucleotide, forming a chain extension of the target sequence comprising one or more copies of a polynucleotide sequence complementary to the template sequence connected through cleavable polynucleotide sequences, cleaving the extension into fragments at the cleavable polynucleotide sequences, denaturing the fragments, hybridizing the fragments with single stranded pattern polynucleotide, and forming a chain extension of the hybridized fragment. The above steps are repeated until the desired number of copies is obtained.

One method (A) for obtaining multiple copies of a primary polynucleotide sequence is represented in FIG. 1.

The single stranded pattern polynucleotide (1) comprised of repeating template sequences (1a) containing restriction endonuclease sites (Δ) is incubated with the primary polynucleotide sequence (2) under temperature and solvent conditions suitable for at least partial hybridization of (1) and (2) to form a duplex (3) in which the 3'—OH of (2) corresponds to the cleavage point in the restriction endonuclease site. Preferably, under the same conditions, duplex (3) reacts with nucleotide triphosphates (NT) by catalysis with template dependent polynucleotide polymerase (TDPP) to extend the primary polynucleotide sequence (2) to form the extended duplex (4). Under preferably the same conditions duplex (4) reacts with a restriction endonuclease (RE) to form duplex fragments (5) consisting of the template sequence (1a) and the primary polynucleotide sequence (2). Duplex fragments (5) dissociate to give multiple copies of the single stranded primary polynucleotide sequence (2) which reenter the cycle.

In this method the single stranded pattern polynucleotide (1) can also include nucleotide sequences bound to its 3' and 5' ends, and these sequences may be connected to form a ring. Usually, when additional sequences are bound to the single stranded pattern polynucleotide, the repeating template sequences will be made up of only two or three, preferably three, of the four natural nucleotides, dA or A, dT or U, or dG or G, and dC or C, or derivatives thereof. Under this circumstance only the two or three corresponding complementary nucleotide triphosphates or derivatives thereof are included in the polymerization reaction.

A method for analyzing for a polynucleotide analyte involves causing the analyte to effect formation of primary polynucleotide sequence from which multiples can be formed by the method of this invention and detecting these copies. One method (B) for effecting formation of a primary polynucleotide sequence by the polynucleotide analyte is depicted in FIG. 2.

A polynucleotide analyte (6) containing a target polynucleotide sequence (6a) is denatured and then hybridized with excess single stranded pattern polynucleotide (1) having a portion of its template sequence (1a) complementary to the target polynucleotide sequence (6a). The resulting hybrid (7) is then treated with a restriction enzyme (RE) to form a free hydroxy at the 3' end of the target polynucleotide sequence (6b). This target polynucleotide sequence, which forms as a duplex (8) with at least a portion of the single stranded pattern polynucleotide (1), is dissociated from the duplex (8) and is hybridized to another molecule of single stranded pattern polynucleotide (1) to form the new duplex (9). The duplex (9) reacts with nucleoside triphosphates (NT) by catalysis with template-dependent polynucleotide polymerase (TDPP) to extend target polynucleotide sequence (6b) and form an extended duplex (10). Under preferably the same conditions, duplex (10) reacts with a restriction endonuclease (RE) to form duplex fragments (5) which can dissociate into primary polynucleotide sequence (2) as illustrated in method (A).

Another method (C) for effecting formation of a primary polynucleotide sequence by the presence of a polynucleotide analyte is depicted in FIG. 3.

The polynucleotide analyte (6) is first treated with a restriction enzyme (RE) that cuts the target polynucleotide sequence (6a) to produce duplex (11) containing the target polynucleotide sequence (6b) terminating in a 3'-hydroxy group. This duplex is then dissociated, and the cleaved target polynucleotide sequence is hybridized with excess single stranded pattern polynucleotide (1) to form duplex (9). Duplex (9) is extended according to method (B) for forming a primary polynucleotide sequence.

In another method (D) (see FIG. 4) for effecting formation of a primary polynucleotide sequence by the presence of a polynucleotide analyte, duplex (11) is dissociated and rehybridized with a single stranded pattern polynucleotide (12) which contains at least one template sequence (1a) and a binding polynucleotide sequence (12a) at its 3' end that is complementary to target sequence (6b). Preferably, (12) is cyclic and in no case can it be susceptible to chain extension by template dependent polynucleotide polymerase in the absence of a cleavage agent.

The resulting duplex (13) reacts with nucleotide triphosphates (NT) by catalysis with template-dependent polynucleotide polymerase (TDPP) to extend the target polynucleotide sequence (6b) to form the extended duplex (14). Duplex (14) reacts with a restriction enzyme (RE) to form duplex fragments (5) which can dissociate into primary polynucleotide sequence (2) as illustrated in method (A). When single stranded pattern polynucleotide (12) contains only one template sequence (1a), it will be necessary to include single stranded pattern polynucleotide (1) that contains at least two template sequences in order to form multiple copies of the primary polynucleotide sequence according to method (A).

In still another method (E) (FIG. 5) for eliciting formation of a primary polynucleotide sequence by presence of a polynucleotide analyte, preferably an RNA analyte, (6') having a sequence of polynucleotides to be identified (6a') the analyte is dissociated into single strands, if it is not already single stranded. It is then hybridized with a primer polynucleotide (15) comprised of a primary polynucleotide sequence (2) with its 3' end bound to a binding polynucleotide sequence (15a).

After formation of hybrid (16), the hybrid is cut by a restriction enzyme to give the primary polynucleotide sequence (2) with a free 3'—OH suitable for formation of multiple copies according to method (A).

Another method (F) (FIG. 6) for effecting formation of a primary polynucleotide sequence as a result of the presence of a polynucleotide analyte requires a single stranded pattern polynucleotide (18) comprised of a binding polynucleotide sequence (18a) connected at its 5' end to an oligomer of template sequences (1a). A duplex (11) containing a target polynucleotide sequence (6b) ending in a 3'-hydroxyl is produced in response to the presence of a polynucleotide analyte according to Methods (B) or (C). The duplex is denatured and the sequence (6B) is hybridized with the single stranded pattern polynucleotide (18). The resulting hybrid (19) reacts with nucleotide triphosphates (NT) by catalysis with template-dependent polynucleotide polymerase (TDPP) to extend the target polynucleotide sequence (6b) and form an extended duplex (20). Duplex (20) reacts with a restriction endonuclease (RE) to form duplex fragments (5) which can dissociate into the primary polynucleotide sequence (2) as illustrated in Method (A). In addition duplex (21) is found which can dissociate and hybridize with single stranded pattern polynucleotide (18) to reform hybrid (19).

In carrying out the method an aqueous medium will be employed. Other polar cosolvents may also be employed, usually oxygenated organic solvents of from 1-6, more usually from 1-4, carbon atoms, including alcohols, ethers and the like. Usually these cosolvents will be present in less than about 70 weight percent, more usually in less than about 30 weight percent.

The pH for the medium will usually be in the range of about 4.5 to 9.5, more usually in the range of about 5.5-8.5, and preferably in the range of about 6-8. The pH and temperature are chosen and varied, as the case may be, so as to provide for either simultaneous or sequential hybridization of the target sequence with the single stranded pattern polynucleotide, extension of the target sequence, cleavage of the extension into fragments at the cleavable polynucleotide sequences, reversible denaturation of the fragments, hybridization the fragments with single stranded pattern polynucleotide, and extension of the hybridized fragments. In some instances, a compromise will be made between these considerations depending on whether the above steps are performed sequentially or simultaneously. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another.

Moderate temperatures are normally employed for carrying out the method and desirably constant temperatures during the period for conducting the method. A constant temperature will usually be selected near the melting temperature of the complex of primary polynucleotide sequence and the template sequence. The option to utilize a constant temperature is a benefit realized in the present method that arises because the length of the primary polynucleotide sequence and the newly formed copies thereof are identical. The temperatures for the method will generally range from about 20° to 90° C., more usually from about 30° to 70° C. preferably 37° to 50° C. However, the temperature can be varied depending on whether the above steps are carried out sequentially or simultaneously. For example, relatively low temperatures of from about 20° to 40° C. can be employed for the chain extension and cleavage steps, while denaturation and hybridization can be carried out at a temperature of from about 40° to 80° C.

The time period for carrying out the method of the invention will generally be long enough to achieve a desired number of copies of the primary polynucleotide sequence. This, in turn, depends on the purpose for which the amplification is conducted, such as, for example, an assay for a polynucleotide analyte. Generally, the time period for conducting the method will be from about 5 to 200 min. As a matter of convenience it will usually be desirable to minimize the time period. In general, the time period for a given degree of amplification can be shortened, for example, by selecting concentrations of nucleoside triphosphates, sufficient to saturate the template dependent nucleotide polymerase and by increasing the concentrations of template-dependent polynucleotide polymerase. A particularly critical factor is the efficiency of the means to cleave site specific cleavage sequences. It will generally be desirable to select conditions that maximize the cleavage rates, for example, by use of a restriction enzyme having a high turn over and optimizing its concentration. Another critical factor in reducing the time period is the number of template sequences present in the single stranded pattern polynucleotide.

Provided at least two template sequences are present, the number of copies of polynucleotide sequence that are formed will increase exponentially with each extension. Preferably, at least three template sequences are present whereupon the number of copies doubles with each extension of the primary polynucleotide sequence. More preferably at least five template sequences are present and the number of copies triples with each extension. In general the number of copies present after each extension should multiply by about $(n+1)/2$ where n is the number of template sequences in the single stranded pattern polynucleotide.

The concentration of the target polynucleotide sequence which is to be copied can be as low as one or two molecules in a sample but will generally vary from about $10^2$ to $10^{10}$, more usually from about $10^3$ to $10^8$. The concentration of the single stranded pattern polynucleotide sequence will usually depend on the number of copies desired, and the rate at which such copies are formed will normally determine the concentration of the other reagents and the number of template sequences in the single stranded pattern polynucleotides.

The final concentration of each of the reagents will normally be determined empirically to optimize the number of the copies of the target sequence.

The concentration of the single stranded pattern polynucleotide and the deoxynucleoside triphosphates in the medium can vary widely; preferably, these reagents are present in an excess amount. The deoxynucleoside triphosphates will usually be present in $10^{-6}$ to $10^{-2}$M, preferably $10^{-5}$ to $10^{-3}$M. The single stranded pattern polynucleotide will usually be present in at least $10^{-12}$M, preferably $10^{-10}$M, more preferably at least about $10^{-8}$M.

The concentration of the template-dependent polynucleotide polymerase and the means for cleaving the site specific cleavable sequence, which is usually a restriction endonuclease and any cofactors thereof in the medium can also vary substantially. These reagents may be present in as low as $10^{-12}$M but may be present in a concentration at least as high or higher than the concentration of the single stranded pattern polynucleotide. The primary limiting factor being the cost of the reagents, which are usually enzymes.

The order of combining of the various reagents to form the combination may vary. Generally, a target polynucleotide sequence located at the 3' terminus of a polynucleotide is obtained. This may be combined with a pre-prepared combination of single stranded pattern polynucleotide sequence, nucleoside triphosphates, template-dependent polynucleotide polymerase, and cleaving agent. However, simultaneous addition of the above, as well as other step-wise or sequential orders of addition, may be employed.

The concentration and order of addition of reagents and conditions for the method are governed generally by the desire to maximize the number of copies of the primary polynucleotide sequence and the rate at which such copies are formed.

One aspect of the present invention concerns the determination or detection of a polynucleotide analyte terminating in, or caused to be terminated in, a 3'-hydroxy nucleotide. The polynucleotide analyte will generally be present in a sample suspected of containing the polynucleotide analyte. The method comprises providing in combination in an aqueous medium either sequentially or simultaneously one or more of the polynucleotide analyte, an exogeneously added single stranded pattern polynucleotide capable of hybridizing with the polynucleotide analyte, nucleoside triphosphates, and template-dependent polynucleotide polymerase. The medium is incubated under conditions for either sequentially or simultaneously hybridizing at least a target sequence in the polynucleotide analyte with single stranded pattern polynucleotide, forming an extension of the target sequence along the template, cleaving the extension into fragments, denaturing the fragments by hybridizing the fragments with single stranded pattern polynucleotide, and forming an extension of the fragments. The above steps are repeated under the reaction conditions until a detectible number of fragments are obtained. Thereafter, the fragments, or fragments complementary thereto, are detected and the presence of the fragments indicates the presence of the polynucleotide analyte in the sample.

Prior to providing the combination, the sample can be incubated sequentially (1) with reagents for modifying the 3' end of any polynucleotide in the sample to prevent free 3' ends from reacting with the template-dependent polymerase and (2) with a restriction enzyme capable of producing a hydroxyl group at the 3' end of the polynucleotide analyte to be determined. The reagents for modifying the 3' end of a polynucleotide can comprise an enzyme capable of catalyzing the reaction of the polynucleotide 3'-hydroxyl group. Examples of such an enzyme are polynucleotide ligases from any source such as *E. coli* bacteria ligases, T4 phage DNA ligase, mammalian DNA ligase, and the like, terminal deoxynucleotidyl transferases, T4 RNA ligase, and so forth. The ligases referred to above additionally can include an oligonucleotide terminated at the 3' end with a group that does not react to provide chain extension by the template-dependent polynucleotide polymerase. The terminal transferase can include a dideoxynucleotide triphosphate, methylated nucleotide triphosphate, and the like. Such reagents and reactions are well known in the art for other applications and further detailed discussion is not necessary here.

The pH, temperature, solvent, and time considerations will be similar to those described above for the amplification method. Generally, conditions are chosen for either sequentially or simultaneously hybridizing the polynucleotide analyte with the single stranded pattern polynucleotide, forming an extension along the pattern polynucleotide, cleaving the extension into fragments, reversibly denaturing the fragments, hybridizing the fragments with single strand pattern polynucleotide, and forming an extension of the fragments. The concentration of polynucleotide analyte which can be assayed will be similar to those described above for the concentration of the target polynucleotide sequence.

While the concentrations of the various reagents will generally be determined by the concentration range of interest of the polynucleotide analyte, the final concentration of each of the reagents will normally be determined empirically to optimize the sensitivity of the assay over the range of interest. The concentration of the other reagents in an assay generally will be determined following the same principles as set forth above for the amlification methods. The primary consideration is that a sufficient number of copies of a primary polynucleotide sequence be produced in relation to the polynucleotide analyte sequence so that such copies can be readily detected and provide an accurate determination of the polynucleotide analyte.

After the medium is incubated either simultaneously or sequentially under the above conditions any fragments present are detected. The presence of the fragments indicates the presence of the polynucleotide analyte in the sample. The fragments can be detected in numerous ways. Essentially any method for detection of nucleic acids can be utilized in detecting the fragments formed in the assay method in the present invention. Alternatively, any method for detection of pyrophosphate formed during the polymerization can be utilized. Any standard method for detecting double strand nucleic acid can be used such as, for example, precipitation of the single strand material with trichloracetic acid and measurement of light absorption of the solution, intercalation of a dye, such as ethidium bromide, and the like, followed by spectroscopic measurement, measurement of changes in hyperchromicity, optical rotation measurements, nucleic acid probe hybridization methods, and the like. Any of the above detection methods can be utilized in conjunction with a preliminary chromatographic separation step to separate double strand fragments the size of the hybridized or unhybridized primary polynucleotide sequence from higher and lower molecular weight material in the medium. The above procedures are well known in the art and will not be described in great detail but rather will be described in a summary fashion in the following paragraphs.

One method for detecting nucleic acids is to employ nucleic acid probes. This method generally involves immobilization of the target nucleic acid on a solid support such as nitrocellulose paper, cellulose paper, diazotized paper, or a nylon membrane. After the target nucleic acid is fixed on the support, the support is contacted with a suitably labelled probe nucleic acid for about two to forty-eight hours. After the above time period, the solid support is washed several times at elevated temperatures to remove unbound probe. The support is then dried and the hybridized material is detected by autoradiography or by colorimetric methods.

One method utilizing probes is described in U.S. patent application Ser. No. 773,386, filed Sept. 6, 1985, the disclosure of which is incorporated herein by reference. The method comprises combining in an assay medium the sample and first and second polynucleotide reagents complementary to the nucleic acid fragment. Each of the first and second reagents hybridize with a different region of nucleic acid fragment. The first reagent contains means for rendering the first reagent non-covalently polymerizable. The second reagent contains means for rendering the second reagent detectable. The sample and the first and second reagents are combined in the assay medium under conditions for polymerizing the first reagent wherein the second reagent becomes bound to the polymerized first reagent only when the DNA fragment is present in the sample. A determination is then made as to whether the second reagent has become bound to the polymerized first reagent.

In the present method, the primary polynucleotide sequence can be labeled with a ligand by having present a ligand substituted nucleotide triphosphate in the combination of reagents. The template sequence can be labeled with a second ligand. The complex of these two sequences that is formed in the method can be detected by causing the complex to bind to a surface to which is bound a receptor for one of the ligands. A receptor for the other ligand that is labeled with a detectable group such as an enzyme or fluorophore can then be caused to bind to the other ligand in proportion to the amount of the complex that binds to the surface.

Another method for detecting the nucleic acid fragments involves dyes possessing an affinity for DNA or RNA. Exemplary of such dyes are DNA intercalating agents, which are generally well known compounds and are, for the most part, commercially available. Representative of such agents are acriflavine, acriflavine hydrochloride, and like acridine derivatives, and ethidium halides such as ethidium bromide.

The above method can also be applied to the determination of the presence of an RNA analyte in a sample suspected of containing such RNA analyte. The RNA polynucleotide analyte is provided by combining in an aqueous medium the sample, a single stranded DNA primer comprising a deoxynucleic acid sequence containing a restriction site and capable of hybridizing with the RNA sequence, and a restriction enzyme capable of cleaving the primer at the restriction site when the primer is hybridized with the RNA sequence. The combination is incubated for a time sufficient to permit cleaving to occur under conditions for cleaving the hybridized primer at the restriction site. Such conditions are similar to those described above for cleaving the site specific cleavage sequences. The cleaved primer can then serve as the target sequence in the above method.

The DNA primer can be cyclic or can be terminated at its 3' end by a group incapable of reacting in a reaction catalyzed by the template-dependent polynucleotide polymerase.

One embodiment of the present invention is a method of producing multiple polynucleotide molecules as a function of the presence of a target sequence of nucleotides in a polynucleotide sample. The method comprises combining the polynucleotide sample either simultaneously or wholly or partially sequentially with one or more of (1) means to cause the target sequence to terminate in a 3' hydroxy group when the target sequence does not already terminate in such group, (2) single stranded pattern polynucleotide comprising a binding polynucleotide sequence complementary to substantially all of the target sequence and a site specific cleavage sequence joined at the 5' end of the binding polynucleotide sequence wherein the 5' end of the site specific cleavage sequence is joined to the 3' end of the template sequence (4) nucleoside triphosphates, (5) template-dependent polynucleotide polymerase, and (6) means for cleaving the sequence complementary to the site specific cleavage sequences when hybridized with the site specific cleavage sequences. The combining is carried out under conditions which promote wholly or partially, either sequential or simultaneous denaturation of the target sequence when the target sequence is double stranded, hybridization of the target sequence with the template, extension of the target sequence by template-dependent polynucleotide polymerase to produce a duplex, cleavage of the extension in the duplex into fragments, denaturation of the duplex, hybridization of the fragments with single stranded pattern polynucleotide, and extension of said fragments. The above steps are repeated until the desired number of copies is obtained.

Another embodiment of the present invention is a method for determining the presence of a polynucleotide analyte in a sample suspected of containing said polynucleotide analyte. The method comprises combining in an aqueous medium either wholly or partially sequentially or simultaneously (1) said sample, (2) means for obtaining from the polynucleotide analyte a target sequence and for terminating the sequence in a 3'—OH group, (3) single stranded pattern polynucleotide comprised of a sequence complementary to the target sequence joined at its 5' end to a multiply repeated sequence of at least 12 nucleotides, said repeated sequence, when hybridized to its complementary sequence and incubated with a restriction enzyme, promoting cleavage of the complementary sequence to form restriction fragments, (4) deoxynucleoside triphosphates, (5) a DNA dependent nucleotide polymerase for extending the target sequence to provide said complementary sequence, and (6) a restriction endonucleases for forming the restriction fragments. The combining is carried out under conditions for either wholly or partially sequentially or simultaneously obtaining the target sequence from the polynucleotide analyte, hybridizing the target sequence to the single stranded pattern oligonucleotide, extending the target sequence to form the complementary sequence, cleaving the complementary sequence into fragments, denaturing the hybridized duplex of the complementary sequence and the repeated sequence, hybridizing the fragments with single stranded pattern polynucleotide, and extending the fragments to form complementary sequences. The method further includes detecting cleaved complementary sequence. The presence of the cleaved complementary sequence indicates the presence of the polynucleotide analyte in said sample.

Another embodiment of the present method is directed to determining the presence of a target sequence of nucleotides in a polynucleotide analyte in a sample suspected of containing the polynucleotide analyte. The method comprises combining said sample either wholly or partially sequentially or simultaneously with one or more of (1) means capable of causing the target sequence to be terminated in a 3'—OH group, (2) a single stranded pattern oligodeoxynucleotide template comprised of a sequence complementary to the target sequence, the sequence bonded at its 5' end to a multiply repeating sequence of at least 12 nucleotides which, when hybridized to a complementary sequence allows cleavage of said complementary sequence to form fragments, (3) deoxynucleoside triphosphates, (4) DNA dependent DNA polymerase and (5) a restriction enzyme for cleaving the complementary sequence when hybridized to the cleavage promoting sequence. The method further comprises incubating the individual components and mixtures formed therefrom under conditions which promote either wholly or partially sequential or simultaneous (a) denaturation of the target sequence when the target sequence is double stranded, (b) hybridization of the target sequence with the template, (c) extension of the target sequence by DNA dependent DNA polymerase to produce a duplex containing the complementary sequence, (d) cleavage of the complementary sequence in the duplex into fragments, (e) melting of the duplex, and (f) hybridization of the fragments with single stranded pattern polynucleotide, and extension of the fragments by DNA dependent DNA polymerase to produce a duplex containing the complementary sequence and repeating the above steps. Thereafter, the complementary sequence or fragments of the template produced during cleavage of said complementary sequence are detected. The presence thereof indicates the presence of the analyte in said sample.

Another aspect of the present invention involves a polydeoxynucleotide comprising a single stranded DNA oligomer consisting of from about 3 to 100, preferably 6 to 50, oligonucleotide units and at least one restriction site. Each oligodeoxynucleotide unit consists of an oligodeoxynucleotide template containing at least one restriction site and having from about 8 to 100, preferably 10 to 50 nucleotides. Preferably, the monomer units are identical. The oligodeoxynucleotide can be cyclic or non-cyclic and is preferably cyclic. The DNA oligomer can be bonded at its 3' end to a single stranded polynucleotide binding sequence consisting of at least about 15 nucleotides. Preferably, the oligomer and any polynucleotide sequence connecting the oligomer and the binding sequence are composed of two or three, preferably three, members selected from the group of nucleotides and deoxynucleotides or a corresponding derivative thereof. Preferably, the nucleotides are selected from three members of the group consisting of A and dA or a derivative thereof, U and dT or a derivative thereof, G and dG or a derivative thereof and C and dC or a derivative thereof. When cyclic, the 5' end of the DNA oligomer can be connected directly or through a polynucleotide sequence to the 3' end of the binding sequence to form a ring. The oligonucleotide can preferably contain from about 3 to 100, preferably 6 to 50, template sequences, and the template sequences can preferably each consist of from about 8 to 100, preferably 10 to 50, more preferably 10 to 20, nucleotides. Reporter groups can be bound to the DNA oligomer, preferably, one reporter group per monomer unit. The reporter groups include radioactive molecules, fluorescers, chemiluminescers, small organic groups of molecular weight of from about 17 to 1000 such as biotin, $NH_2$, OH, SH, fluorescein, etc., and the like.

Various techniques can be employed for preparing a single stranded pattern polynucleotide in accordance with the present invention. In an approach for preparing an oligomer of a template sequence, the single stranded pattern polynucleotide can be prepared by enzymatic ligation. An appropriate oligonucleotide which is identical to the template or upon ligation with itself forms a template sequence, can be synthesized by standard automated techniques. It is then enzymatically ligated together, for example, by T4 ligase, to produce the single stranded pattern polynucleotide. Oligomers of the desired length can then be isolated, for example, by polyacrylamide gel electrophoresis or high performance liquid chromatography (HPLC). Frequently, the 3' end of the oligomer will be modified to prevent reaction with template dependent DNA polymerase or to append a binding sequence, preferably catalyzed by a ligase. The 3'-end can also be modified by ligation of a dideoxynucleotide or a ribonucleotide followed by oxidation of the ribose with periodate followed by reductive amination of the resulting dialdehyde with borohydride and a bulky amine such as aminodextran.

In another approach the single stranded polynucleotide can be prepared by recombinant DNA technology. In another approach, the single stranded pattern polynucleotide can be synthesized entirely by standard solid phase automatable methods as, for example, by use of phosphoamidates. In this method the group anchoring the synthetic sequence to the solid support can be released at the last step and can serve to prevent reaction of the 3' end with DNA polymerase. Alternatively, the single stranded pattern polynucleotide may be left covalently bonded at the 3' end to a solid support and thus blocked. The solid support can be, for example, a bead, sheet, particle, or the like composed of synthetic or natural material such as, for example, organic polymer, glass, inorganic polymer and the like. This material may be subsequently extented at its 5' end and increased in the number of its template units by chemical or enzymatic ligation with other oligonucleotides. In a preferred approach the single stranded pattern polynucleotide can be prepared by standard cloning techniques, for example, by use of the cyclic single stranded M13 phage. In this approach the synthetic oligomer terminating in cleaved restriction sites is inserted at the corresponding restriction site into the polylinker region of M13. Where desired, a binding polynucleotide sequence can be similarly inserted. The phage is then cloned and harvested.

An important consideration in whatever approach is utilized to prepare the single stranded pattern polynucleotide is that the single stranded pattern polynucleotide be free from complementary polynucleotide sequences. The presence of complementary sequences will result in random initiation of chain extension.

A particularly preferred composition for use in the method of the present invention is a cyclic single stranded pattern polydeoxynucleotide having at least three contiguous, preferably, identical, template sequences of polydeoxynucleotides. Each template sequence contains at least one restriction site. These sequences and any sequence connecting the binding polynucleotide sequence with the template sequence oligomer lack one member of the group of nucleotides comprising adenine (A) and deoxyadenine (dA), guanidine (G) and deoxyguanidine (dG), cytidine (C) and deoxycytidine (dC), and thymidine (T) and deoxythymidine (dT) or a corresponding derivative thereof. The absence of one of the bases together with the use of only the nucleoside triphosphates complementary to the remaining three bases in the deoxynucleotide polymerase catalyzed reactions considerably reduces or eliminates random initiation of chain extension at polynucleotide sequences outside the template sequence oligomer and any sequence connecting it to the binding polynucleotide sequence. Thus, chain extension can occur along the template sequences, but random hybridization at some other point on the cyclic pattern polynucleotide or polynucleotide analyte will continue only for a very short distance until a nucleotide is encountered which is complementary to the nucleotide absence in the deoxynucleoside triphosphate mixture.

The template sequence in the above cyclic pattern polynucleotide preferably contains from eight to one hundred nucleotides. The cyclic pattern polynucleotide usually contains from about 3 to 50, preferably at least 6 template sequences. A preferred cyclic pattern polynucleotide for use in the present method is a synthetic sequence cloned into M13, $\phi$X174, or the like.

As a matter of convenience, the reagents employed in the present invention can be provided in a kit in packaged combination with predetermined amounts of reagents for use in obtaining multiple copies of a primary polynucleotide sequence or for use in assaying for a polynucleotide analyte in a sample. For example, a kit useful in the present method can comprise in packaged combination with other reagents a composition such as that described above. The kit can further include in the packaged combination nucleoside triphosphates such as deoxynucleoside triphosphates, e.g., deoxyadenosine triphosphate (dATP), deoxyguanosine triphosphate (dGTP), deoxycytidine triphosphate (dCTP) and deoxythymidine triphosphate (dTTP). The kit can further include template-dependent polynucleotide polymerase and also means for cleaving the site specific cleavage sequences or the sequences complementary thereto or both. Where the target polynucleotide sequence is RNA, the kit can further include in packaged combination a single stranded DNA primer. The DNA primer comprises a nucleic acid sequence capable of hybridizing with the RNA and containing a restriction site. The primer is terminated at its 3' end by a group incapable of reacting in a chain extension in the presence of template-dependent polynucleotide polymerase. Where a restriction enzyme is used for cleaving the cleavable sequences that is different from the restriction enzyme used for providing that the target sequence terminate in a 3' hydroxyl group, the kit can further include in packaged combination the restriction enzyme for causing the target sequence or complementary sequence to terminate in a 3' hydroxy group. For assays for the determination of a polynucleotide analyte the kit can include one or more of the above in packaged combination with other reagents for conducting an assay and reagents for detecting DNA fragments as described above.

The relative amounts of the various reagents in the kits can be varied widely to provide for concentrations of the reagents which substantially optimize the production of, and the rate of production of, multiple copies of the primary polynucleotide sequence. For kits to be used in conducting an assay the reagents can be provided to further substantially optimize the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention.

EXAMPLES

The invention is demonstrated further by the following illustrative examples.

EXAMPLE 1

Polymerase mediated DNA target amplification was demonstrated in an experiment using circular M13 as a single stranded pattern polynucleotide. A 17 base synthetic target DNA polynucleotide was annealed to complementary single stranded pattern polynucleotide containing two non-identical template sequences M13mp19 DNA and elongated with Klenow fragment polymerase and all four deoxynucleoside triphosphates (dNTPs). The restriction endonucleases Eco RI, Bam HI, and Hind III specifically cleaved the elongated double stranded DNA under polymerase reaction conditions. The amount of primary polynucleotide fragments produced could be substantially increased by thermal cycling of the reaction. This cycling was accomplished by boiling the reaction mixture, allowing DNA strand renaturation in the presence of excess pattern polynucleotide template at a lower temperature, and continuing the polymerization/cutting by the addition of fresh enzymes. Primary polynucleotide fragments were observed after gel electrophoresis under denaturing conditions. No fragments were observed in control reactions where target DNA was absent.

Nucleic Acids:

M13mp19 single stranded DNA (Lot No. 63102) and the 17 base DNA (Lot No. 62101) were purchased from Bethesda Research Labs (BRL), Gaithersburg, MD. The 17 base DNA has the nucleotide sequence 5' GTAAAACGACGGCCAGT 3'. This DNA functioned as a target polynucleotide sequence in the system described here and is referred to herein also as the target polynucleotide.

Enzymes:

Klenow fragment DNA-dependent DNA polymerase (Lot No. NM 92818; supplied as an FPLCpure ™ 7.2 units/$\mu$l solution) was purchased from Pharmacia Inc., Piscataway, NJ. The restriction endonucleases Eco RI (Lot No. 411L1, 10 units/$\mu$l), Hind III (Lot No. 51111, 10 units/$\mu$l), and Bam HI (Lot No. 461D1, 10 units/$\mu$l) were purchased from BRL.

Buffers and Other Reagents:

Klenow polymerase buffer (10×) was 70 mM Tris-HCl (pH=7.5), 70 mM $MgCl_2$, and 500 mM NaCl. The four deoxynucleoside triphosphates (dATP, dGTP, dCTP, and dTTP) were purchased as 100 mM solutions from Pharmacia Inc. Water was sterile filtered Milli-Q reagent grade ™. All chemicals were reagent grade or better. Electrophoresis reagents were purchased from Bio-Rad Inc., Richmond, CA. $\alpha$-$^{32}$P dTTP (3000 Ci/mmol; 10 mCi/ml) was purchased from New England Nuclear Corp., Boston, MA.

Hybridization Reaction Conditions:

1.0 $\mu$l of 17 base DNA (2 ng/m 1; 2 ng≃180 fmoles), 20.5 $\mu$l of M13mp19 single stranded DNA (10 $\mu$g/41 $\mu$l; 4 $\mu$g≃2.1 pmoles) and 6.0 $\mu$l of 10× Klenow polymerase buffer were added to a sterile 1.5 ml Eppendorf tube, mixed by vortex, and spun briefly to recover the volume in the bottom of the tube. The mixture was incubated at 60° C. for 5 minutes and then allowed to cool to room temperature (approximately 30 minutes). After cooling, 21.5 $\mu$l of $\alpha$-$^{32}$P dTTP, 4.0 $\mu$l of dNTPs (0.4 mM each), and 4.0 $\mu$l of DTT (0.1M) were added to the reaction. A 4.0 $\mu$l aliquot was removed from the reaction as a zero time point before the addition of enzymes. In parallel with the target containing reaction described above, an identical control reaction was run substituting 1.0 $\mu$l of water for the target polynucleotide sequence.

The Amplification Reaction:

For the first cycle, 1.0 $\mu$l of Klenow polymerase and 1.0 $\mu$l of each of the three restriction endonucleases (Eco RI, Hind III, and Bam HI) were added to the reaction. The reactions were incubated at 37° C. for 2 minutes and then transferred to a boiling water bath for 5 minutes to effect denaturation of the fragments produced. Previous experiments had shown that under the present conditions, primary polynucleotide elongation beyond the three restriction endonuclease sites was complete after 2 minutes. After denaturation, the tubes were placed at 60° C. for 10 minutes and then 37° C. for 5 minutes. The reactions were spun briefly to recover all the liquid into the bottom of the tube, and then a 4.0 $\mu$l aliquot was withdrawn for analysis (cycle #1). Fresh enzymes were added the second polymerization cycle was started. This procedure was repeated for a total of four cycles.

Results:

Aliquots taken after each cycle from both the tubes containing the target polynucleotide and the control were analyzed by 20% polyacrylamide gel electrophoresis under denaturing conditions (8M urea; 56° C.) Radioactively labeled DNA markers were co-electrophoresed to estimate the sizes of the bands observed.

Table III summarizes the densitometry data obtained from an analysis of the gel autoradiogram. A comparison is also shown in this Table between the values observed for the relative peak intensities and those expected theoretically.

TABLE III

| Cycle # | Relative amount of 21 mer fragment | | Relative amount 30 mer fragment | |
|---|---|---|---|---|
| | Observed | Expected | Observed | Expected |
| 1 | 1 | 1 | 1 | 1 |
| 2 | 2.05 | 2 | 1.72 | 3 |
| 3 | 2.99 | 3 | 1.59 | 6 |
| 4 | 3.88 | 4 | 4.45 | 10 |

*Normalized to the amount of material observed after the first cycle.

It should be emphasized that no detectable bands were observed in any of the reactions where target DNA was absent. Hence, the assay is completely dependent on target DNA. Moreover, as can be clearly seen from Table III, amplification of the amount of primary polynucleotide is occurring through successive cycles.

EXAMPLE 2

A repeating polydeoxynucleotide of sequence:

| 5" | CGGGGAATTC |
| | TTTAAATATTCC |
| | TTTAAACCTACC |
| | TTTAAACCTACC |
| | TTTAAACCTACC |
| | TTTAAACCTACC |
| | TTTAAACCTACC |
| | TTTAAACCTACC |
| | TTTAAACCTACC |
| | TTTAAATATTCCGAATTCACTGGCCG 3' (120 mer) | and an oligodeoxynucleotide of sequence 5' CGGCCAGTGAATTCGGA 3' (17 mer) were synthesized by the phosphoramidite method. A portion of the 17 mer (50 ng, 8.9 pmoles) was radioactively labeled at the 5' end with $\alpha$-$^{32}$P ATP(Lot #2387-299 NEN, 3000 Ci/mmole, 10 m Ci/ml) T4 polynucleotide kinase using standard methods (Maxam, A. and Gilbert, W. (1980) Methods in Enzymology 65, 499) to follow the subsequent enzymatic reactions. The radioactive 17 mer was purified by NENSORB ™ chromatography (DuPont/New England Nuclear) using the protocol provided by the supplier.

The 120 mer (1 $\mu$g=25 pmoles) was incubated with a ten-fold molar excess (1.4 $\mu$g=250 pmoles) of 17 mer including all of the radioactively labeled 17 mer described above at 60° C. for 5 minutes and then slowly cooled over 30 minutes to 37° C. in a volume of 20.2 $\mu$l in 1.3× Klenow buffer (1× Klenow buffer is 7 MM Tris-HCl (pH 7.5), 7 mM $MgCl_2$, 50 mM NaCl). To this cooled reaction mix was added 2 μl of a solution of 0.4 mM dATP, dCTP, dGTP, dTTP (final conc.=32 μM of each dNTPs), 1.8 μl of 0.1M dithiothreitol (final conc.=7.2 μM) and 7.2 units of Klenow polymerase (Pharmacia Lot #NM 92818) in a final concentration of 1× Klenow buffer. This reaction was incubated at 37° C. for 30 minutes. An additional 7.2 units of Klenow polymerase (1 μl volume) was added and the reaction was continued at 37° C. for one hour.

The reaction products were ethanol precipitated by the addition of 375 μl of 0.3M Na Acetate (pH 5.4) and 1.1 ml ethanol (−20° C.), followed by spinning at 15,000 g's for 30 minutes. The precipitated DNA was then resuspended in 25 μl of H₂O and reprecipitated with 1 ml of 100% ethanol (4° C.) and centrifugation as above. The supernatant was removed and the precipitated DNA pellet dried under vacuum.

The pellet was resuspended in 17 μl of distilled water, and 2 μl of Eco RI restriction enzyme buffer (final concentration=50 mM Tris (pH 8.0), 10 mM MgCl₂, 100 mM NaCl) and 1 μl (20 unit) Eco RI restriction endonuclease (Bethesda Research Labs, final concentration=1 unit/μl). The reaction was allowed to proceed for 1 hour at 37° C. 1 μl of this reaction was analyzed by 20% polyacrylamide/8M urea gel electrophoresis to confirm complete digestion of Eco RI restriction sites. The remainder of the reaction products (19 μl) was purified by NENSORB ™ chromatography and evaporated to dryness.

Bacteriophage M13mp19 replicative form DNA (Garisch-Perran, C., Vieira, J., and Messing, J. (1985) *Gene* 33, 103–119) was digested (1.3 μg) with Eco RI restriction enzyme and frozen to inactivate the restriction enzyme. 135 ng of this linearized M13mp19 was added to the total Klenow polymerizatin/Eco RI restriction products above, with 0.5 mM ATP, 1 unit of T4 DNA ligase (Bethesda Research Labs, Lot #51131), 66 mM Tris-HCl (pH 7.6), 6.6 mM MgCl₂, and 10 mM dithiothreitol in a final reaction volume of 20 μl. Reaction was performed at 12° C. for 18 hours.

Ten (10) μl of this reaction mix in five 2 μl aliquots was incubated with *E. coli* JM 101 bacterial cells rendered competent for DNA transformation using standard protocols (Maniatis, et al. "Molecular Cloning," Cold Spring Harbor Laboratory, [1982]). The five transformations were plated on YT media petri dishes and incubated overnight at 37° C. (Maniatis, pp. 320–321). These petri plates were screened in duplicate with nitrocellulose filter replicas by standard methods (Benton, W. D. and R. W. Davis (1977) *Science* 196, 180). The radioactive probe used for screening was the starting 120 mer which was 5'³²P labeled to an approx. specific activity of 2×10⁷ cpm/μg.

Autoradiography of the dried filters showed approximately 100 M13mp19 infected JM 101 colonies which hybridized to the radioactive probe in the five petri plates. Seven of these positive clones were picked at random. These were sequenced by Sanger dideoxy sequencing (Sanger, F., et al. (1980) *J. Mol. Biol.* 143, 161) and found each to contain a single insertion in the same orientation of the expected Eco RI bracketed repeating polynucleotide sequence. This clone is hereinafter referred to as the "M13mp19 Dra I clone."

Using this sequence (or a multimer of it) directly adjacent to a target DNA sequence has a number of advantages:

1. Only a single restriction endonuclease is needed to generate a number of fragments.

2. Six of the fragments are of the same sequence and length, resulting in improvement of the amplification.

3. Since only three bases are needed for polymerization, background from linear DNAs can be greatly reduced by eliminating dGTP (or dCTP if the complement is cloned into the viral strand) from the reaction.

4. A generalized amplification reagent or amplification cassette is possible with this sequence.

EXAMPLE 3

Polymerase Based Elongation Of Primer Upon The M13mp19 Dra I Clone Template

A 23 base long oligodeoxynucleotide primer of sequence 5'-GTAAAACGACGGCCAGTGAATTC-3' was hybridized to the M13mp19 Dra I clone in a volume of 50 microliters. The total amount of primer in the hybridization was 0.021 pmoles; the total amount of M13mp19 Dra I clone was 2.1 pmoles. Hybridization was done under temperature and buffer conditions previously described.

Four parallel polymerization reactions were performed at 37° C. The polymerase used was either 14.4 units of Klenow polymerase (Pharmacia, Lot # NM92818) in two separate reaction volumes or 2.75 units T7 polymerase (United States Biochemical Corporation, Lot # 51255) in the two remaining reactions. 40 units of restriction endonuclease Dra I was included in one of the Klenow and one of the T7 polymerizations. Only three deoxynucleoside triphosphates were included in the polymerizations, dATP, dCTP and dTTP, each at final concentration of 32 μM.

Aliquots were taken from the reaction at 0, 2, 4, 6, 10, 20 and 30 minutes. These were mixed with an appropriate volume of 95% formamide and bromophenol blue, xylene cyanol dyes and electrophoresed on 20% denaturing acrylamide gels. Autoradiography of the gels revealed the expected 12 base long oligonucleotide bands plus higher moleculer weight multimers of the 12 mer when both a polymerase and Dra I restriction enzyme were included in the reaction. In the presence of polymerase, but without the addition of Dra I, no radioactive product is evident on the autoradiogram. Table Iv lists the integrated areas for each of the fragment bands obtained with T7 polymerase elongation in the presence of Dra I. Densitometry was performed with a ZEINEH soft laser densitometer model SL-504-XL (Biomed Instruments Inc., Fullerton, Calif.). No bands were observed within the gel in the absence of Dra I restriction endonuclease.

TABLE IV

Integrated areas obtained from laser densitometry of the gel autoradiogram bands

| Incubation Time (min) | Fragment Sizes | | | |
|---|---|---|---|---|
| | 12 | 24 | 36 | 48 |
| 0 | 0 | 0 | 0 | 0 |
| 2 | 0 | 0 | 0 | 0 |
| 4 | 56 | 10 | 0 | 0 |
| 6 | 159 | 74 | 29 | 0 |
| 10 | 532 | 131 | 43 | 6 |
| 20 | 871 | 127 | 34 | 6 |
| 30 | 664 | 800 | 360 | 213 |

Although the foregoing invention has been described in some detail by way of illustration and example for purposes of clarity of understanding, it will be obvious that certain changes and modifications may be practiced within the scope of the appended claims.

What is claimed is:

1. A method of producing multiple copies of a primary polynucleotide sequence located at the 3' terminus of a polynucleotide, which comprises:
   (a) forming in the presence of nucleoside triphosphates and template-dependent polynucleotide polymerase an extension of a primary polynucleotide sequence hybridized with a template sequence of a single stranded pattern polynucleotide comprising two or more identical template sequences each containing one or more site specific cleavage sequences,
   (b) cleaving into fragments said extension at cleavable polynucleotide sequences in the presence of means for specifically cleaving said cleavable polynucleotide sequences when said extension is hybridized with said site specific cleavage sequences,
   (c) dissociating said fragments, said fragments comprising a primary polynucleotide sequence,
   (d) hybridizing said fragments with said single stranded pattern polynucleotide, and
   repeating steps (a)-(d) above wherein steps (a)-(d) are conducted simultaneously or wholly or partially sequentially.

2. The method of claim 1 wherein said primary polynucleotide sequence is DNA.

3. The method of claim 1 wherein said single stranded pattern polynucleotide comprises an oligomer of at least three of an identical template sequence.

4. The method of claim 3 wherein said single stranded pattern polynucleotide is cyclic.

5. The method of claim 3 wherein said site specific cleavage sequences contained in said template sequences are all identical.

6. The method of claim 3 wherein said oligomer is terminated at the 3' end by a chemical group or solid support incapable of reacting in a chain extension reaction of said oligomer catalyzed by said template dependent polynucleotide polymerase.

7. The method of claim 1 wherein said template sequence is 8 to 100 nucleotides in length.

8. The method of claim 1 wherein said site specific cleavage sequence is a restriction endonuclease site and said means for specifically cleaving said cleavable polynucleotide sequences comprises a restriction endonuclease.

9. The method of claim 1 wherein said template-dependent polynucleotide polymerase is a DNA polymerase and said deoxynucleoside triphophates are dATP, dGTP, dCTP, and dTTP.

10. The method of claim 1 wherein said method is carried out at a substantially constant temperature.

11. A method of producing multiple copies of a primary polynucleotide sequence located at the 3' terminus of a polynucleotide, which comprises:
   (a) forming in the presence of nucleoside triphosphates and template-dependent polynucleotide polymerase an extension of a primary polynucleotide sequence hybridized with a template sequence of a single stranded pattern polynucleotide comprising two or more template sequences each containing one or more site specific cleavage sequences.
   (b) cleaving into fragments said extension at cleavable polynucleotide sequences in the presence of means for specifically cleaving said cleavable polynucleotide sequences when said extension is hybridized with said site specific cleavage sequences,
   (c) dissociating said fragments, said fragments comprising a primary polynucleotide sequence.
   (d) hybridizing said fragments with said single stranded pattern polynucleotide, and
   repeating steps (a)-(d) above wherein steps (a)-(d) are conducted simultaneously or wholly or partially sequentially and wherein the number of said copies of said primary polynucleotide sequence formed for each of said extension is increased by at least a factor of three.

12. The method of claim 1 wherein the 3' end of said template sequences in said single stranded pattern polynucleotide is connected to a polynucleotide sequence complementary to a polynucleotide analyte in a sample suspected of containing said polynucleotide analyte.

13. The method of claim 1 wherein said single stranded pattern polynucleotide is at least part of a cyclic polynucleotide.

14. The method of claim 1 wherein said nucleoside triphosphates are selected from three members of the group consisting of dATP, dTTP, dGTP, and dCTP and derivatives thereof.

15. The method of claim 1 wherein said template sequences and the sequences connecting said template sequences consist of a continuous sequence of nucleotides selected from three members of the group consisting of A and dA, U and dT, C and dC, and G and dG and derivatives thereof.

16. The method of claim 15 wherein said derivatives are selected from the group consisting of methylated nucleotides and nucleotides labeled with a reporter group.

17. The method of claim 16 wherein said reporter group is selected from the group consisting of biotin, fluorescers, chemiluminescers, and small organic molecules.

18. A method of producing multiple copies of a primary polynucleotide sequence as the result of the presence of a target polynucleotide sequence located at the 3' terminus of a polynucleotide, which comprises:
   (a) forming in the presence of nucleoside triphosphates and template-dependent polynucleotide polymerase an extension of a target polynucleotide sequence hybridized with a binding polynucleotide sequence of a single stranded pattern polynucleotide comprising said binding polynucleotide sequence and two or more copies of a template sequence each containing one or more site specific cleavage sequences,
   (b) cleaving into fragments said extension at cleavable polynucleotide sequences in the presence of means for specifically cleaving said cleavable polynucleotide sequences when said extension is hybridized with said site specific cleavage sequences,
   (c) dissociating said fragments, wherein said fragments comprise said primary polynucleotide sequence
   (d) hybridizing said fragments with said single stranded pattern polynucleotide,
   (e) forming in the presence of said nucleoside triphosphates and said template dependent polynucleotide polymerase an extension of said fragments hybridized with said single stranded pattern polynucleotide, and
   (f) repeating steps (b)-(e) above wherein steps (b)-(e) are conducted simultaneously or wholly or partially sequentially.

19. The method of claim 18 wherein said target polynucleotide sequence is DNA.

20. The method of claim 18 wherein said single stranded pattern polynucleotide comprises an oligomer of at least three of said template sequences.

21. The method of claim 18 wherein said single stranded pattern polynucleotide is cyclic.

22. The method of claim 18 wherein said site specific cleavage sequences contained in said template sequences are all identical.

23. The method of claim 18 wherein said binding polynucleotide sequence is connected to said template sequence by a site specific cleavage sequence.

24. The method of claim 20 wherein said oligomer is terminated at the 3' end by a group incapable of reacting in a chain extension reaction of said oligomer catalyzed by said template dependent polynucleotide polymerase.

25. The method of claim 18 wherein said template sequence is 8 to 100 nucleotides in length.

26. The method of claim 18 wherein said site specific cleavage sequence is a restriction endonuclease site and said means for specifically cleaving said cleavable polynucleotide sequences comprises a restriction endonuclease.

27. The method of claim 18 wherein said template-dependent polynucleotide polymerase is a DNA polymerase and said nucleoside triphosphates are dATP, dGTP, dCTP, and dTTP.

28. The method of claim 18 wherein said method is carried out at a substantially constant temperature.

29. The method of claim 18 wherein said single stranded pattern polynucleotide comprises 5 to 50 template sequences connected by one or more site specific cleavage sequences.

30. A method of producing multiple polynucleotide molecules as a function of the presence of a target sequence of nucleotides present in a polynucleotide sample, which method comprises:
   combining either wholly or partially sequentially or simultaneously (1) said polynucleotide sample containing said target sequence, (2) means to cause said target sequence to terminate in a free 3'—OH group when said target sequence does not already terminate in a free 3'-OH group, (3) single stranded pattern polynucleotide comprising a binding polynucleotide sequence complementary to substantially all of said target sequence, joined at its 5' end to two or more identical template sequences each containing site specific cleavage sequence, (4) nucleoside triphosphates, (5) template-dependent polynucleotide polymerase, and (6) means for cleaving a sequence complementary to said site specific cleavage sequences when hybridized with said site specific cleavage sequence,
   said combining being carried out under conditions which promote either wholly or partially sequentially or simultaneously (a) denaturation of said target sequence when said target sequence is double stranded, (b) hybridization of said target sequence with said binding polynucleotide sequence, (c) extension of said target sequence by template dependent polymerization to produce a duplex, (d) cleavage of said extension in said duplex into fragments, (e) reversible denaturation of said fragments, (f) hybridization of said fragments with single stranded pattern polynuceotide, and (g) extension of said hybridized fragments by template dependent polymerization to produce a duplex, and
   repeating steps (d)-(g).

31. The method of claim 30 wherein said single stranded pattern polynucleotide is present in excess amount over the amount of said target sequence and said conditions include an essentially constant temperature.

32. The method of claim 30 wherein said binding sequence and said template sequence are the same.

33. The method of claim 30 wherein said polynucleotide sample is DNA and said means to cause said target sequence to terminate in a 3'—OH group is a restriction enzyme.

34. The method of claim 30 wherein said site specific cleavage sequence in said single stranded pattern polynucleotide is a sequence capable of cleavage by a restriction endonuclease.

35. The method of claim 34 wherein said restriction endonuclease is the same as the means to cause said target sequence to terminate in a 3'—OH group.

36. The method of claim 30 wherein said site specific cleavage sequence includes a sequence complementary to the target sequence.

37. The method of claim 30 wherein the 5' end of said template sequence is bonded with or without an intervening polynucleotide sequence to the 3' end of said binding sequence to form a ring.

38. The method of claim 30 wherein said template sequence is about 8–100 nucleotides long and said single stranded pattern polynucleotide comprises an oligomer containing 2–100 of said template sequences.

39. The method of claim 30 wherein said single stranded pattern polynucleotide is terminated at the 3' end by a group that is incapable of reacting in a reaction catalyzed by said template dependent polynucleotide polymerase.

40. The method of claim 30 wherein said polynucleotide sample is RNA and said means to cause said target sequence to terminate in a 3'—OH group includes (1) a single stranded DNA primer comprising a deoxynucleic acid sequence containing a restriction site and capable of hybridizing with said target sequence, and (2) a restriction endonuclease capable of cleaving said primer at said restriction site when said primer is hybridized with said RNA sequence.

41. The method of claim 40 wherein said primer is cyclic or is terminated at its 3' end by a group incapable of reacting in a reaction catalyzed by said template-dependent polynucleotide polymerase.

42. The method of claim 30 wherein said polynucleotide sample is selected from the group consisting of the genomes of viruses, bacteria, molds, and fungi, and fragments thereof.

43. The method of claim 30 wherein said template dependent polynucleotide polymerase is DNA polymerase.

44. The method of claim 30 wherein said single stranded pattern polynucleotide is a linear oligonucleotide.

45. The method of claim 30 wherein said single stranded pattern polynucleotide is at least part of a cyclic polynucleotide.

46. The method of claim 30 wherein said polynucleotide sample is double stranded DNA and said target sequence is caused to terminate in a free 3'—OH group by cleaving said DNA with a restriction endonuclease.

47. The method of claim 30 wherein said polynucleotide sample is a DNA-RNA heteroduplex formed by hybridizing RNA with a single stranded oligodeoxynucleotide complementary to said binding polynucleotide sequence and terminated at the 3' end by a group that is incapable of reacting in a reaction catalyzed by said template-dependent polynucleotide polymerase, said heteroduplex providing for cleavage by a restriction endonuclease of at least said oligodeoxynucleotide with formation of said target sequence terminating in a 3'-hydroxyl.

48. The method of claim 30 wherein terminal 3'—OH groups of said polynucleotide sample are rendered unreactive with said template dependent polynucleotide polymerase prior to combining said polynucleotide sample with said means to cause said target sequence to terminate in a 3'—OH group.

49. The method of claim 30 wherein said nucleoside triphosphates are selected from three members of the group consisting of dATP, dTTP, dGTP, and dCPT and derivatives thereof.

50. The method of claim 49 wherein said template sequence and polynucleotide sequences joining said template sequences consists of a continuous sequence of nucleotides selected from three members of the group consisting of A and dA, U and dT, C and dC, G and dG and derivatives thereof.

51. A method of producing multiple copies of a primary polynucleotide sequence located at the 3' terminus of a polynucleotide which comprises:
    providing in combination either wholly or partially sequentially or concomitantly (1) said primary polynucleotide sequence hybridized with single stranded pattern polynucleotide, (2) single stranded pattern polynucleotide comprising two or more identical template sequences each containing site specific cleavage sequences, (3) nucleoside triphosphates, (4) template-dependent polynucleotide polymerase, and (5) means for specifically cleaving cleavable polynucleotide sequences complementary to site specific cleavage sequences when said cleavable polynucleotide sequences are hybridized with said site specific cleavage sequences and
    incubating said combination under conditions for either wholly or partially sequentially or concomitantly (a) forming an extension of said primary polynucleotide sequence comprising one or more copies thereof, (b) cleaving said extension at said cleavable polynucleotide sequences into primary polynucleotide sequences, (c) dissociating said hybridized extension, (d) hybridizing said primary polynucleotide sequences with said single stranded pattern polynucleotide, and repeating at least steps (a) and (b) above.

52. A method of producing multiple copies of a primary polynucleotide sequence as the result of the presence of a target polynucleotide sequence located at the 3' terminus of a polynucleotide which comprises:
    providing in combination either wholly or partially sequentially or concomitantly (1) said target polynucleotide sequence hybridized to a single stranded pattern polynucleotide comprising a binding sequence complementary to said target polynucleotide sequence and one or more copies of a template sequence complementary to said primary polynucleotide sequence each containing two or more site specific cleavage sequences, (2) single stranded pattern polynucleotide, (3) nucleoside triphosphates, (4) template-dependent polynucleotide polymerase, and (5) means for specifically cleaving cleavable polynucleotide sequences complementary to said site specific cleavage sequences when said cleavable polynucleotide sequences are hybridized with said site specific cleavage sequences and
    incubating said combination under conditions for either wholly or partially sequentially or concomitantly (a) forming an extension of said target sequence comprising one or more of said copies of said primary polynucleotide sequence connected through said cleavable polynucleotide sequences, (b) cleaving said extension at said cleavable polynucleotide sequences into said target sequence and primary polynucleotide sequences, (c) dissociating said hybridized extension, (d) hybridizing said primary polynucleotide sequence with said single stranded pattern polynucleotide, and (e) forming an extension of said primary polynucleotide sequence comprising one or more copies of said primary polynucleotide sequence, and
    repeating steps (b)–(e).

53. A method for producing multiple copies of a primary polydeoxynucleotide sequence complementary to a template sequence, which comprises:
    providing in an aqueous medium either simultaneously or wholly or partially sequentially a mixture comprising (1) said primary polydeoxynucleotide sequence; (2) a cyclic single stranded pattern polydeoxynucleotide comprising an oligomer of at least three identical template sequences each containing one or more restriction endonuclease sites, said oligomer consisting of only three independent nucleotides selected from the group consisting of deoxynucleotides or corresponding derivatives thereof; (3) the three deoxynucleotide triphosphates complementary to said deoxynucleotides corresponding to the bases in said primary polydeoxynucleotide sequence; (4) DNA dependent DNA polymerase; and (5) one or more restriction endonucleases capable of cleaving a duplex consisting of said single stranded pattern polydeoxynucleotide and single stranded DNA complementary to said pattern polydeoxynucleotide, said cleaving occurring at said restriction sites and only when said single stranded pattern polydeoxynucleotide is bound to said complementary single stranded DNA; and
    incubating said mixture under conditions for either simultaneously or wholly or partially sequentially hybridizing said primary polydeoxynucleotide with said single stranded pattern polydeoxynucleotide, extending said primary polydeoxynucleotide along said single stranded pattern polydeoxynucleotide to form said duplex, cleaving said duplex at said restriction sites, dissociating said primary polydeoxynucleotide from said template sequence, and rehybridizing said primary polydeoxynucleotide with said single stranded pattern polydeoxynucleotide.

54. The method of claim 53 wherein said primary polydeoxynucleotide sequence is formed in response to the presence of a polynucleotide analyte in a sample suspected of containing said polynucleotide analyte which further comprises the steps of: prior to said providing (1) treating said polynucleotide analyte to provide a single stranded target sequence terminating in a 3'-hydroxy group, (2) incubating said target sequence with reagents required to provide said primary polydeoxynucleotide sequence, and subsequent to said incubating (3) detecting said multiple copies of said primary polydeoxynucleotide sequence.

55. The method of claim 54 wherein said polynucleotide analyte is treated in step (1) with a restriction endonuclease to provide said 3'-hydroxy group.

56. The method of claim 55 wherein said polynucleotide analyte is first denatured and then incubated with a single stranded binding polydeoxynucleotide sequence containing a restriction site recognized by said endonuclease.

57. The method of claim 56 wherein said single stranded binding polydeoxynucleotide sequence is a part of said single stranded pattern polydeoxynucleotide.

58. The method of claim 54 wherein said single stranded pattern polydeoxynucleotide further comprises a binding polydeoxynucleotide sequence complementary to said target sequence and connected at its 5' end to the 3' end of said oligomer only by combinations of said three deoxynucleotides.

59. The method of claim 54 wherein said reagents for incubating said target sequence to provide said primary polydeoxynucleotide sequence include (1) a binding polynucleotide sequence complementary to said target sequence connected at its 5' end to the 3' end of said template sequence either directly or by a combination of said three nucleotides, and (2) a restriction endonuclease capable of cleaving at said cleavage site.

60. A method of producing multiple copies of a primary polydeoxynucleotide sequence complementary to a template sequence which comprises:
  (a) forming in the presence of three members selected from the group consisting of deoxynucleoside triphosphates or corresponding derivatives thereof and DNA-dependent DNA polymerase an extension of a primary polydeoxynucleotide sequence hybridized with a template sequence of a cyclic single stranded pattern polydeoxynucleotide comprising an oligomer having at least three identical template sequences each containing one or more restriction endonuclease sites and a sequence of nucleotides complementary to said three members and derivatives thereof,
  (b) cleaving into fragments said extension at said restriction endonuclease sites in the presence of one or more restriction endonucleases capable of cleaving at said restriction endonuclease sites only when said extension is hybridized with said single stranded pattern polynucleotide,
  (c) dissociating said fragments,
  (d) hybridizing said fragments with said single stranded pattern polydeoxynucleotide, and
  repeating steps (a)–(d) above wherein steps (a)–(d) are conducted simultaneously or wholly or partially sequentially.

61. The method of claim 60 wherein said primary polydeoxynucleotide sequence is formed in response to the presence of a polynucleotide analyte in a sample suspected of containing said polynucleotide analyte wherein prior or simultaneously with said forming (1) said polynucleotide analyte is treated to provide a single stranded target sequence terminating in a 3'-hydroxy group and (2) said target sequence is incubated with reagents required to provide said primary polydeoxynucleotide sequence, and (3) wherein subsequent to said repeating said multiple copies of said primary polydeoxynucletide sequence are detected.

62. The method of claim 61 wherein said polynucleotide analyte is treated in step (1) with a restriction endonuclease to provide said 3'-hydroxy group.

63. The method of claim 62 wherein said polynucleotide analyte is first denatured and then incubated with a single stranded binding polydeoxynucleotide sequence containing a restriction site recognized by said endonuclease.

64. The method of claim 63 wherein said single stranded binding polydeoxynucleotide sequence is a part of said single stranded pattern polydeoxynucleotide.

65. The method of claim 61 wherein said single stranded pattern polydeoxynucleotide further comprises a binding polydeoxynucleotide sequence complementary to said target sequence and connected at its 5' end to the 3' end of said oligomer only by combinations of said three deoxynucleotides.

66. The method of claim 61 wherein said reagents for incubating said target sequence to provide said primary polydeoxynucleotide sequence include (1) a binding polynucleotide sequence complementary to said target sequence connected at its 5' end to the 3' end of said template sequence either directly or by a combination of said nucleotides complementary to said three members, and (2) a restriction endonuclease capable of cleaving at said cleavage site.

67. A method for producing multiple copies of a primary polynucleotide sequence as the result of the presence of a target polynucleotide sequence, which method comprises:
  (a) combining (1) a single stranded pattern polynucleotide comprising a binding sequence substantially complementary to said target polynucleotide sequence and two or more identical template sequences each containing one or more restriction sites with (2) said target polynucleotide sequence,
  (b) incubating said combination at a temperature that causes said target polynucleotide sequence to anneal selectively with said binding sequence,
  (c) adding to said combination template-dependent polynucleotide polymerase, a restriction endonuclease for at least one of said restriction sites in said template sequence and, if not already present, nucleoside triphosphates,
  (d) incubating said combination at a temperature sufficient to achieve chain extension of said target polynucleotide sequence and cleavage of said single stranded polynucleotide into fragments,
  (e) denaturing said fragments, said denatured fragments including said primary polynucleotide sequence,
  (f) incubating said combination at a temperature sufficient to anneal said primary polynucleotide sequence to said single stranded pattern polynucleotide, and
  (g) repeating steps (c)–(f) above.

68. A method for producing multiple copies of a sequence of nucleotides, which comprises
  hybridizing a primer polynucleotide sequence to a complementary polynucleotide sequence, said complementary polynucleotide sequence being part of a polynucleotide sequence having multiply repeating units complementary to said sequence of nucleotides to be copied, said multiply repeating units containing only two or three of the nucleotides A and dA or a derivative thereof, C and dC or a derivative thereof, U and dT or a derivative thereof, and G and dG or a derivative thereof, combining the hybridized material with only those nucleoside triphosphates complementary to said two or three nucleotides and with a polynucleotide polymerase, and incubating said combination under conditions for forming an extension of said primer polynucleotide sequence, wherein the above steps are carried out simultaneously or wholly or partially sequentially.

* * * * *